US011136318B2

(12) United States Patent
Strack et al.

(10) Patent No.: US 11,136,318 B2
(45) Date of Patent: Oct. 5, 2021

(54) PROCESSES FOR THE PREPARATION OF ARYL HYDROCARBON RECEPTOR LIGANDS

(71) Applicant: Noramco, LLC, Wilmington, DE (US)

(72) Inventors: Martin Benedict Strack, Kleve (DE); Jasper Kaiser, Nijmegen (NL); Gnel Mkrtchyan, Watkinsville, GA (US); Wen-Chun Zhang, Bogart, GA (US)

(73) Assignee: Noramco, LLC, Wilmington, DE (US)

( * ) Notice: Subject to any disclaimer, the term of this patent is extended or adjusted under 35 U.S.C. 154(b) by 0 days.

(21) Appl. No.: 16/906,363

(22) Filed: Jun. 19, 2020

(65) Prior Publication Data

US 2021/0009579 A1    Jan. 14, 2021

Related U.S. Application Data

(60) Provisional application No. 62/864,737, filed on Jun. 21, 2019.

(51) Int. Cl.
| | | |
|---|---|---|
| *C07D 417/06* | (2006.01) | |
| *C07D 413/06* | (2006.01) | |
| *C07D 403/06* | (2006.01) | |

(52) U.S. Cl.
CPC .................................. *C07D 417/06* (2013.01)

(58) Field of Classification Search
CPC ... C07D 417/06; C07D 413/06; C07D 403/06
See application file for complete search history.

(56) References Cited

U.S. PATENT DOCUMENTS

| 6,916,834 B2 | 7/2005 | DeLuca et al. |
| 7,002,019 B2 | 2/2006 | DeLuca et al. |
| 7,241,900 B2 | 7/2007 | DeLuca et al. |
| 7,419,992 B2 | 9/2008 | DeLuca et al. |
| 8,604,067 B2 | 12/2013 | Song |
| 10,081,610 B2 | 9/2018 | Song et al. |
| 2020/0354353 A1* | 11/2020 | Colabuono .......... C07D 209/12 |

OTHER PUBLICATIONS

Abron et al., "An endogenous aryl hydrocarbon receptor ligand, ITE, induces regulatory T cells and ameliorates experimental colitis," Am J Physiol Gastrointest Liver Physiol., 315(2):G220-G230, (2018).
Cheng et al., "Tryptophan derivatives regulate the transcription of Oct4 in stem-like cancer cells," Nat. Commun., 10(6):7209, (2015).
Grzywacz et al., "A Concise Synthesis of an AHR Endogenous Ligand with the Indolecarbonylthiazole Skeleton," Heterocycles, 60(5):1219-1224, (2003).
Nugent et al., "ITE, a novel endogenous nontoxic aryl hydrocarbon receptor ligand, efficiently suppresses EAU and T-cell-mediated immunity," Invest Ophthalmol Vis Sci., 54(12):7463-7469, (2013).
Quintana et al., "An endogenous aryl hydrocarbon receptor ligand acts on dendritic cells and T cells to suppress experimental autoimmune encephalomyelitis," Proc Natl Acad Sci USA, 107(48):20768-20773, (2010).
Song et al., "A ligand for the aryl hydrocarbon receptor isolated from lung," Proc Natl Acad Sci USA, 99(23):14694-14699, (2002).
Wang et al., "An endogenous aryl hydrocarbon receptor ligand inhibits proliferation and migration of human ovarian cancer cells," Cander Lett., 340(1):63-71, (2013).

* cited by examiner

*Primary Examiner* — Patricia L Morris
(74) *Attorney, Agent, or Firm* — Alston & Bird LLP

(57) ABSTRACT

The present disclosure relates to the preparation of methyl 2-(1H-indole-3-carbonyl)thiazole-4-carboxylate (ITE) and related compounds with high yield, purity, and scalability. The processes apply the use of a Weinreb amide intermediate as a scaffold for the preparation of ITE and structural analogs.

20 Claims, 11 Drawing Sheets

PROCESSES FOR THE PREPARATION OF ARYL HYDROCARBON RECEPTOR LIGANDS

CROSS-REFERENCE TO RELATED APPLICATIONS

This application claims the benefit of priority to U.S. Provisional Patent Application No. 62/864,737, filed on Jun. 21, 2019, the content of which is incorporated by reference herein in its entirety for all purposes.

FIELD

The subject matter described herein relates to the preparation of methyl 2-(1H-indole-3-carbonyl)thiazole-4-carboxylate (ITE) and structural analogs thereof by novel synthetic routes to improve purity, yield, and scalability.

BACKGROUND

The aryl hydrocarbon receptor (Ah receptor or AhR) is a ligand-inducible transcription factor that regulates gene expression. At the cellular level, AhR enables functional interactions with signaling pathways governing cell proliferation and cell cycle, cell morphology, cell adhesion and cell migration. Methyl 2-(1H-indole-3-carbonyl)thiazole-4-carboxylate (ITE) (Song et al. 2002, U.S. Pat. No. 6,916,834) is an endogenous ligand for the Ah receptor. ITE has been used to study AhR-mediated biological processes and to treat disorders, such as cancer (US 2012/0214853, U.S. Pat. No. 8,604,067, Wang et al. 2013, Cheng et al. 2015), obesity (U.S. Pat. No. 7,419,992), inflammatory bowel disease (Abron et al. 2018), and conditions related to an imbalanced immune system (Quintana et al. 2010, Nugent et al. 2013).

While ITE has exhibited useful properties in laboratory-scale biomedical studies since its structural identification in 2003 (U.S. Pat. No. 7,002,019), there is a need for improved preparations of ITE and its structural analogs for use on a large scale in clinical investigations. The subject matter described herein addresses this unmet need.

BRIEF SUMMARY

In certain aspects, the subject matter described herein is directed to a process for the preparation of a compound of Formula I:

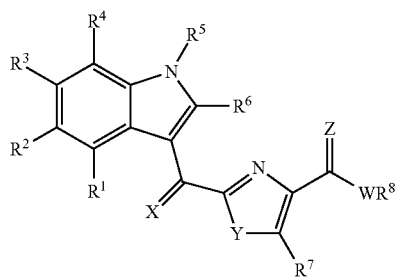

I wherein W, X, Y, and Z are each independently selected from the group consisting of O, S, and NH;

$R^1$, $R^2$, $R^3$, $R^4$, $R^5$, $R^6$, $R^7$, and $R^8$ are each independently selected from the group consisting of hydrogen, deuterium, halo, amino, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, heterocyclyl, and $S(O)_nR^9$ (n=0 to 2, $R^9$ is directly connected to S), wherein $R^9$ is selected from the group consisting of hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, and heterocyclyl;

the process comprising:

contacting a compound of formula (II) with a protecting group in the presence of a nucleophile to prepare a compound of formula (III);

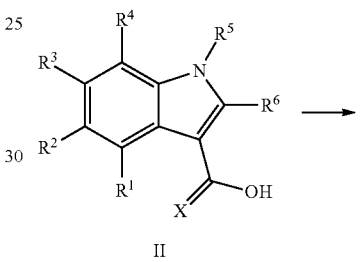

II

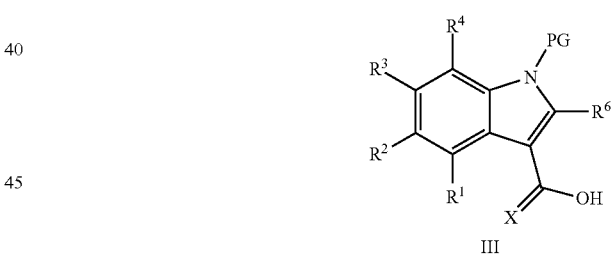

III where PG is the protecting group;

contacting the compound of formula (III) with a halogenating agent, followed by an amine to prepare a compound of formula (IV);

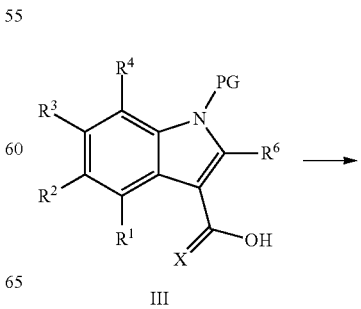

III

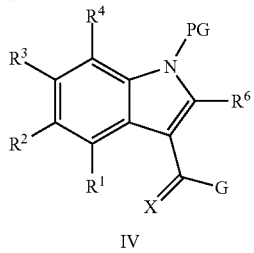

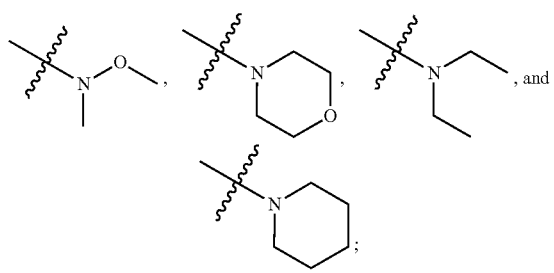

where G is selected from the group consisting of contacting the compound of formula (IV) with a compound of formula (V) in the presence of a base and a solvent to prepare a compound of formula (VI); and

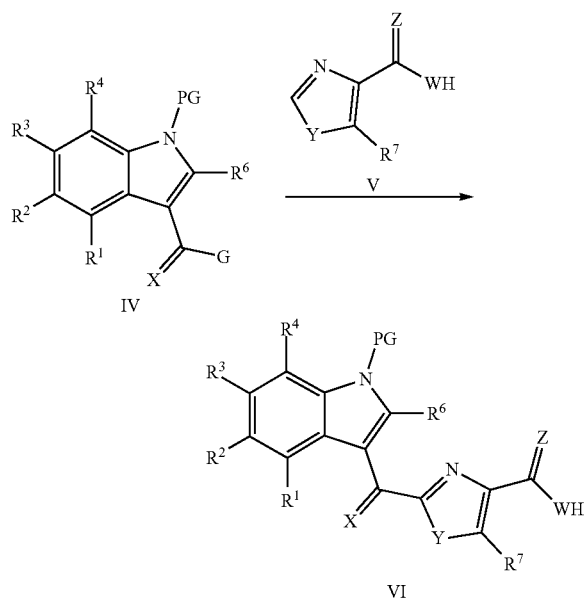

contacting the compound of formula (VI) with an acid; wherein, the compound of Formula I is prepared.

These and other aspects are described fully herein.

DETAILED DESCRIPTION

Figure 1:
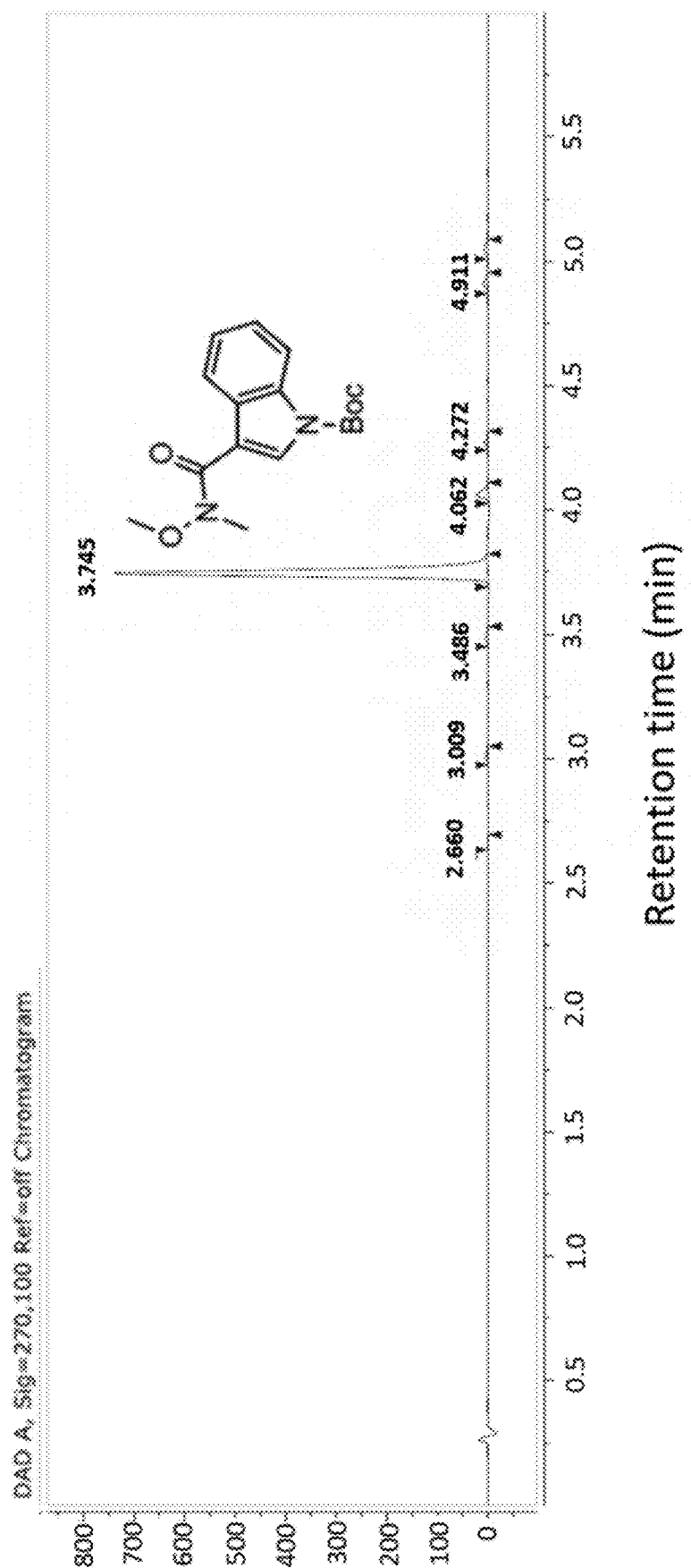
FIG. 1 shows an HPLC chromatogram of tert-Butyl 3-(methoxy(methyl)carbamoyl)-1H-indole-1-carboxylate (47).

Disclosed herein are efficient synthetic routes to prepare methyl 2-(1H-indole-3-carbonyl)thiazole-4-carboxylate (ITE) and structural analogs with improved purity, yield, and scalability. The methods disclosed herein are safe and controllable, employ mild reaction conditions, and utilize readily available reagents.

Known synthetic routes to prepare ITE generally involve condensation and/or cyclization reactions (U.S. Pat. Nos. 7,241,900 and 10,081,610). The intramolecular cyclization reactions typically employed to generate the thiazoline ring in the synthesis of ITE have been shown to limit the overall reaction efficiency, providing low yields (Grzywacz et al. 2003, U.S. Pat. No. 7,002,019). Attempts to scale-up this reaction for industrial applications have resulted in even lower efficiency, generating significant side products and requiring extensive purification. It is understood that this intramolecular cyclization is likely hindered by a neighboring carbonyl group. What is needed is an alternative method that would allow for the production of ITE on a large scale and with high purity.

The presently disclosed reaction conditions use a protected indole to prepare a Weinreb amide intermediate via the corresponding acid halide with a halogenation agent. The Weinreb amide intermediate undergoes nucleophilic acyl substitution with thiazole carboxylic acid to generate an indole thiazole carboxylic acid. After contacting the indole thiazole carboxylic acid with an acid and a solvent, ITE is generated. Surprisingly, the application of the protected indole Weinreb intermediate in the novel synthesis disclosed herein provides a robust substrate for preparation of ITE, without the need for intramolecular cyclization or the use of any harsh solvents. Without wishing to be bound by theory, it is understood that the enhanced nucleophilicity of the metallated thiazole carboxylic acid with the Weinreb amide intermediate enable the efficient synthesis of ITE. Advantageously, the methods described herein provide for large-scale preparation of ITE at high purity, e.g., >95%.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

I. Definitions

As used herein, "ITE" stands for methyl 2-(1H-indole-3-carbonyl)thiazole-4-carboxylate. "ITE" is an endogenous ligand for a receptor named aryl hydrocarbon receptor (Ah receptor, or AhR).

As used herein, "structural analog" or simply "analog" of ITE refers to any compound with a chemical structure similar to that of ITE. Examples of structural analogs include compounds having the same carbon backbone but having different substitutions on the carbons in the carbon backbone or having different degrees of saturation of the carbons in the carbon backbone.

As used herein, "hydroxy," "thiol," "cyano," "nitro," and "formyl" refer, respectively, to —OH, —SH, —CN, —NO$_2$, and —CHO.

As used herein, "alkyl" refers to an unbranched or branched saturated hydrocarbon chain. As used herein, alkyl has 1 to 12 carbon atoms (i.e., $C_1$-$C_{12}$ alkyl), 1 to 8 carbon atoms (i.e., $C_1$-$C_8$ alkyl), 1 to 6 carbon atoms (i.e., $C_1$-$C_6$ alkyl), 1 to 5 carbon atoms (i.e., $C_1$-$C_5$ alkyl), or 3 to 5 carbon atoms (i.e., $C_3$-$C_5$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

As used herein, the terms "halogen," or "halo" refer to atoms occupying group VIIA of the periodic table, such as fluoro, chloro, bromo or iodo. The term "halide" refers to the halogen or halo in a binary compound with hydrogen.

As used herein, "haloalkyl" refers to an alkyl substituted by one or more halo(s).

As used herein, "alkenyl" refers to a group of hydrocarbons containing two (2) to eight (8) carbons, which are linear, branched, cyclic, or in combination thereof, with at least one carbon-to-carbon double bond.

As used herein, "haloalkenyl" refers to an alkenyl substituted by one or more halo(s).

As used herein, "alkynyl" refers to a group of hydrocarbons containing two (2) to eight (8) carbons, which are linear, branched, cyclic, or in combination thereof, with at least one carbon-to-carbon triple bond.

As used herein, "haloalkynyl" refers to an alkynyl substituted by one or more halo(s).

As used herein, "protecting group," and more specifically, "amino protecting group" represents any group commonly used for the protection of amino functions. Such protecting groups are discussed by P. G. M. Wuts in "Protective Groups in Organic Synthesis, 5$^{th}$ Edition" John Wiley and Sons, Inc., New York, ©2014, ISBN-13: 978-1118057483, which is incorporated herein by reference in its entirety. Exemplary protecting groups include alkyl carbamates, moieties of corresponding amides, etc., such as allyl carbamate (Alloc), t-butyl carbamate (BOC), 9-fluorenylmethyl carbamate (FMOC), benzyl carbamate (Cbz), acetamide, chloroacetamide, trifluoroacetamide (TFA), phthalimide, benzylamine, triphenylmethylamine (tritylamine), benzylideneamine, p-toluenesulfonamide, tosylamide, etc.

As used herein, "amino" refers to —NR$_a$R$_b$, wherein R$_a$ and R$_b$, both directly connected to the N, can be independently selected from hydrogen, deuterium, halo, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, heterocyclyl, a nitrogen protective group, or —S(O)$_n$R$_c$(n=0 to 2, R$_c$ is directly connected to S), wherein R$_c$ is independently selected from hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, or heterocyclyl.

As used herein, "alkoxy" refers to an alkyl connected to an oxygen atom (—O-alkyl).

As used herein, "haloalkoxy" refers to a haloalkyl connected to an oxygen atom (—O-haloalkyl).

As used herein, "thioalkoxy" refers to an alkyl connected to a sulfur atom (—S-alkyl).

As used herein, "halothioalkoxy" refers to a haloalkyl connected to a sulfur atom (—S-haloalkyl).

As used herein, "carbonyl" refers to —(CO)—, wherein (CO) indicates that the oxygen is connected to the carbon with a double bond.

As used herein, "alkanoyl (or acyl)" refers to an alkyl connected to a carbonyl group [—(CO)-alkyl].

As used herein, "haloalkanoyl (or haloacyl)" refers to a haloalkyl connected to a carbonyl group [—(CO)-haloalkyl].

As used herein, "thiocarbonyl" refers to —(CS)—, wherein (CS) indicates that the sulfur is connected to the carbon with a double bond.

As used herein, "thioalkanoyl (or thioacyl)" refers to an alkyl connected to a thiocarbonyl group [—(CS)-alkyl].

As used herein, "halothioalkanoyl (or halothioacyl)" refers to a haloalkyl connected to a thiocarbonyl group [—(CS)-haloalkyl].

As used herein, "carbonyloxy" refers to an alkanoyl (or acyl) connected to an oxygen atom [—O—(CO)-alkyl].

As used herein, "halocarbonyloxy" refers to a haloalkanoyl (or haloacyl) connected to an oxygen atom [—O—(CO)-haloalkyl].

As used herein, "carbonylthio" refers to an alkanoyl (or acyl) connected to a sulfur atom [—S—(CO)-alkyl].

As used herein, "halocarbonylthio" refers to a haloalkanoyl (or haloacyl) connected to a sulfur atom [—S—(CO)-haloalkyl].

As used herein, "thiocarbonyloxy" refers to a thioalkanoyl (or thioacyl) connected to an oxygen atom [—O—(CS)-alkyl].

As used herein, "halothiocarbonyloxy" refers to a halothioalkanoyl (or halothioacyl) connected to an oxygen atom [—O—(CS)-haloalkyl].

As used herein, "thiocarbonylthio" refers to a thioalkanoyl (or thioacyl) connected to a sulfur atom [—S—(CS)-alkyl].

As used herein, "halothiocarbonylthio" refers to a halothioalkanoyl (or halothioacyl) connected to a sulfur atom [—S—(CS)-haloalkyl].

As used herein, "Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_6$-$C_{20}$ aryl), 6 to 12 carbon ring atoms (i.e., $C_6$-$C_{12}$ aryl), or 6 to 10 carbon ring atoms (i.e., $C_6$-$C_{10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

As used herein, "cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one $sp^3$ carbon atom (i.e., at least one non-aromatic ring). As used herein, cycloalkyl has from 3 to 20 ring carbon atoms (i.e., $C_3$-$C_{20}$ cycloalkyl), 3 to 12 ring carbon atoms (i.e., $C_3$-$C_{12}$ cycloalkyl), 3 to 10 ring carbon atoms (i.e., $C_3$-$C_{10}$ cycloalkyl), 3 to 8 ring carbon atoms (i.e., $C_3$-$C_8$ cycloalkyl), 3 to 7 ring carbon atoms (i.e., $C_3$-$C_7$ cycloalkyl), or 3 to 6 ring carbon atoms (i.e., $C_3$-$C_6$ cycloalkyl). Monocyclic groups include, for example, cyclopropyl, cyclobutyl, cyclopentyl, cyclohexyl, cycloheptyl and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

As used herein, "heterocyclyl" refers to a saturated or partially unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more (e.g., 1 to 3) oxo (=O) or N-oxide (—O⁻) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_2$-$C_{20}$ heterocyclyl), 2 to 12 ring carbon atoms (i.e., $C_2$-$C_{12}$ heterocyclyl), 2 to 10 ring carbon atoms (i.e., $C_2$-$C_{10}$ heterocyclyl), 2 to 8 ring carbon atoms (i.e., $C_2$-$C_8$ heterocyclyl), 3 to 12 ring carbon atoms (i.e., $C_3$-$C_{12}$ heterocyclyl), 3 to 8 ring carbon atoms (i.e., $C_3$-$C_8$ heterocyclyl), or 3 to 6 ring carbon atoms (i.e., $C_3$-$C_6$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. When the heterocycle ring contains 4- or 6-ring atoms, it is also referred to herein as a 4- or 6-membered heterocycle. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl" when there are two positions for substitution on the same carbon atom. Examples of the spiro-heterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

As used herein, "heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., $C_1$-$C_{20}$ heteroaryl), 3 to 12 ring carbon atoms (i.e., $C_3$-$C_{12}$ heteroaryl), or 3 to 8 carbon ring atoms (i.e., $C_3$-$C_8$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 9-10 membered ring systems, 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzthiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

As used herein, the term "contacting" refers to allowing two or more reagents to contact each other. The contact may or may not be facilitated by mixing, agitating, stirring, and the like.

As used herein, the term "halogenating agent" refers to a compound that can transfer one or more halogen atoms to another compound by contacting it with said compound. Non limiting examples of halogenating agents include thionyl chloride, phosphorous trichloride, oxalyl chloride, methanesulfonyl chloride, trichloromethanesulfonyl chloride, N-chlorosuccinimide, trimethylsilyl chloride, bromotrichloromethane, tetrabutylammonium bromide, and N-bromosuccinimide. As used herein, "chlorination agent" refers to a compound that can transfer one or more chlorine atoms to another compound by contacting it with said compound.

As used herein, "solvent" encompasses any singular solvent or mixture of solvents.

As used herein, the term "nucleophile" is a species that donates an electron-pair to an electrophile to form a covalent bond. Thus, any molecules or ions with a free pair of electrons or at least one pi bond can act as a nucleophile.

Additional definitions may be provided herein.

II. Synthetic Methods

In an aspect, the subject matter described herein is directed to processes for preparing a compound of Formula I:

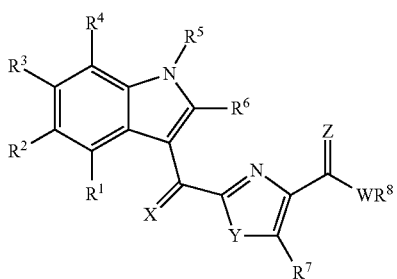

I wherein, W, X, Y, and Z are each independently selected from the group consisting of O, S, and NH;
$R^1$, $R^2$, $R^3$, $R^4$, $R^5$, $R^6$, $R^7$, and $R^8$ are each independently selected from the group consisting of hydrogen, deuterium, halo, amino, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, heterocyclyl, and —$S(O)_nR^9$ (n=0 to 2, $R^9$ is directly connected to S), wherein $R^9$ is selected from the group consisting of hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, and heterocyclyl.

In certain embodiments, useful values of $R^1$, $R^2$, $R^3$, $R^4$, $R^5$, $R^6$, $R^7$, and $R^8$ are each independently selected from the group consisting of hydrogen, $C_1$-$C_6$ alkyl, halo, $C_1$-$C_6$ haloalkyl, and alkoxy. In certain embodiments, useful values of $R^1$, $R^2$, $R^3$, $R^4$, $R^5$, $R^6$, $R^7$, and $R^8$ are each independently selected from the group consisting of hydrogen, methyl, ethyl, and propyl. In certain embodiments, W, X, Y, and Z are each independently O or S. In one aspect, X, Z, and W are each O and Y is S.

In an aspect, the subject matter described herein is directed to processes for preparing a compound of Formula (III), the process comprising, contacting a compound of formula (II) with a protecting group in the presence of a nucleophile;

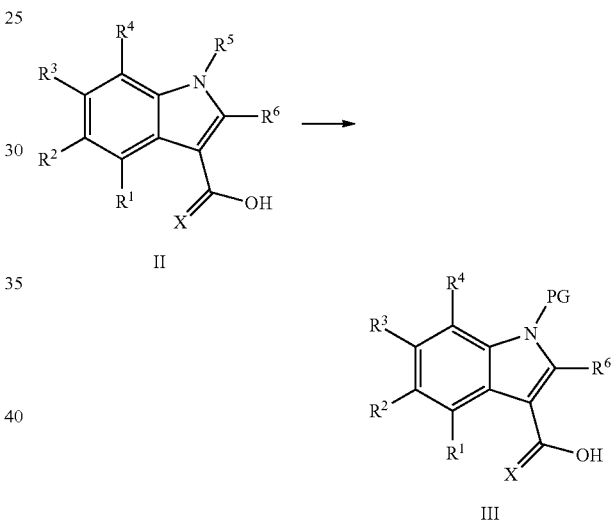

where PG is a protecting group.

In certain embodiments, the contacting a compound of formula (II) with a protecting group in the presence of a nucleophile to prepare a compound of formula (III) is conducted at a temperature of from about 0° C. to about 85° C., from about 10° C. to about 75° C., from about 20° C. to about 70° C., from about 30° C. to about 70° C., from about 35° C. to about 65° C., or from about 40° C. to about 60° C. In certain embodiments, the contacting a compound of formula (II) with a protecting group in the presence of a nucleophile to prepare a compound of formula (III) is conducted at about 25° C.

In certain embodiments, the protecting group (PG) is selected from the group consisting of allyl carbamate (Alloc), t-butyl carbamate (BOC), 9-fluorenylmethyl carbamate (FMOC), benzyl carbamate (Cbz), acetamide, chloroacetamide, trifluoroacetamide (TFA), phthalimide, benzylamine, triphenylmethylamine (tritylamine), benzylideneamine, p-toluenesulfonamide, and tosylamide. In certain embodiments, the protecting group is t-butyl carbamate (BOC).

In certain embodiments, the nucleophile is selected from the group consisting of 1,4-Diazabicyclo[2.2.2]octane (DABCO), quinuclidine, N-Methylpiperidine, N-methylmorpholine, and 4-dimethylaminopyridine (DMAP). In certain embodiments, the nucleophile is 4-dimethylaminopyridine (DMAP).

In certain embodiments, contacting the compound of formula (II) with a protecting group in the presence of a nucleophile is in the presence of a solvent (s-a). In certain embodiments, the solvent (s-a) is selected from the group consisting of dimethylformamide (N,N-dimethylformamide) (DMF), dimethyl sulfoxide (DMSO), pyridine, dioxane, dichloromethane, perfluorohexane, α,α,α-trifluorotoluene, pentane, hexane, cyclohexane, methylcyclohexane, decalin, carbon tetrachloride, freon-11, benzene, dicholoromethane, toluene, triethyl amine, carbon disulfide, isopropyl acetate, diisopropyl ether, diethyl ether (ether), t-butyl methyl ether, chloroform, ethyl acetate, 1,2-dimethoxyethane (glyme), 2-methoxyethyl ether (diglyme), tetrahydrofuran (THF), dichloromethane, 2-butanone, acetone, hexamethylphosphoramide, N-methylpyrrolidinone, nitromethane, acetonitrile, sulfolane, and propylene carbonate. In certain embodiments, the solvent (s-a) is selected from the group consisting of ethyl acetate, dimethylformamide (DMF), dichloromethane, toluene, dimethyl sulfoxide (DMSO), isopropyl acetate, acetonitrile, and acetone. In certain embodiments, the solvent (s-a) is dimethylformamide (DMF).

In certain embodiments, contacting the compound of formula (II) with a protecting group in the presence of a nucleophile is in the presence of a base (b-a). In certain embodiments, the base (b-a) is selected from the group consisting of 1,8-diazabicyclo[5.4.0]undec-7-ene (DBU), NaHCO$_3$, Na$_2$CO$_3$, triethylamine (TEA), potassium tert-butoxide, sodium tert-butoxide pyridine, potassium carbonate, sodium hydroxide, sodium hydride, potassium hydride, N,N-diisopropylethylamine (DIPEA), phosphazene bases, such as t-Bu-P4, lithium diisopropylamide (LDA), silicon-based amides, such as sodium and potassium bis(trimethylsilyl)amide (NaHMDS and KHMDS, respectively), lithium tetramethylpiperidide (LiTMP), and 2,6-di-tert-butylpyridine. In certain embodiments, the base (b-a) is selected from the group consisting of diisopropylethylamine, pyridine, triethylamine, and 2,6-Di-tert-butylpyridine. In certain embodiments, the base (b-a) is triethylamine.

In the contacting a compound of formula (II) with a protecting group in the presence of a nucleophile to prepare a compound of formula (III) is conducted for a period of time of about 0.5 hours, about 1 hour, about 2 hours, about 3 hours, about 4 hours, or more and/or up to about 6 hours, about 7 hours, about 8 hours, about 9 hours, about 10 hours, about 15 hours, about 20 hours, about 25 hours, about 30 hours, about 40 hours or more.

In certain embodiments, the contacting a compound of formula (II) with a protecting group in the presence of a nucleophile to prepare a compound of formula (III) is capable of reaching a percent yield of formula (III) of at least about 10%, about 20%, about 30%, about 40%, about 50%, about 60%, about 70%, about 80%, or about 90% and/or up to about 90%, about 91%, or about 95%.

In certain embodiments, the process produces the compound of Formula (III) having a purity above about 92%, above about 93%, above about 94%, above about 95%, above about 96%, above about 97%, above about 98% or above about 99%.

In certain embodiments, the protecting group is present in an amount from 0.5 equivalents to about 10 equivalents, about 2 to about 20 equivalents, or about 1 equivalents to about 5 equivalents. In certain embodiments, the protecting group is present in about 1, 2, 3, 4, 5, 6, 7, 8, 9, or 10 equivalents.

In certain embodiments, the base (b-a) is present in an amount from about 0.5 to about 10 equivalents, about 2 to about 15, or about 1 to about 5 equivalents. In certain embodiments, the base (b-a) is present in an amount from about 2 to about 6 equivalents. In certain embodiments, the base (b-a) is present in an amount of about 1, 2, 3, 4, 5, or 6 equivalents.

In certain embodiments, the nucleophile is present in an amount from about 0.01 to about 10 equivalents, about 0.02 to about 15 equivalents, or about 0.05 to about 2 equivalents. In certain embodiments, the nucleophile is present in an amount of about 0.05, 0.07, 0.08, 0.09, 0.1, 0.11, 0.12, 0.13, 0.14, 0.15, 0.2, 0.5, 1, 2, 3, 5, or 7 equivalents.

In certain embodiments, the solvent (s-a) used in contacting the compound of formula (II) with a protecting group in the presence of a nucleophile is present from about 1 vol to about 15 vol, about 2 vol to about 7 vol, about 3 vol to about 12 vol, about 4 vol to about 11 vol. In certain embodiments, the solvent (s-b) is present in about 5 vol, about 6 vol, about 7 vol, about 8 vol, about 9 vol, about 10 vol, about 11 vol, or about 12 vol.

In certain embodiments, the compound of formula (III) is not isolated.

In another aspect, the subject matter described herein is directed to processes for preparing a compound of formula (IV), the processes comprising contacting a compound of formula (III) with a halogenating agent, followed by an amine;

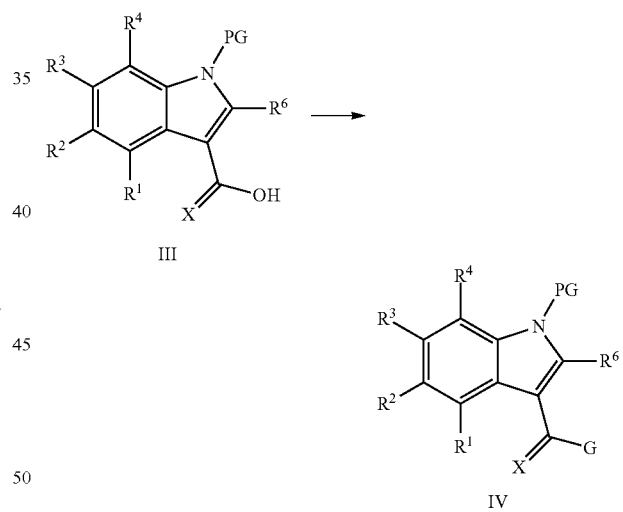

where G is selected from the group consisting of

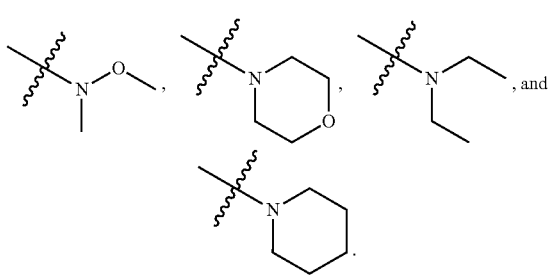

In certain embodiments, the halogenating agent is selected from the group consisting of thionyl chloride ($SOCl_2$), phosphorous trichloride ($POCl_3$), oxalyl chloride (($COCl)_2$), methanesulfonyl chloride, trichloromethanesulfonyl chloride, N-chlorosuccinimide, trimethylsilyl chloride, bromotrichloromethane, tetrabutylammonium bromide, and N-bromosuccinimide. In certain embodiments, the halogenating agent is selected from the group consisting of thionyl chloride ($SOCl_2$), phosphorous trichloride ($POCl_3$), and oxalyl chloride (($COCl)_2$) In certain embodiments, the halogenating agent is oxalyl chloride (($COCl)_2$).

In certain embodiments, the compound of formula (III) is contacted with a halogenating agent, followed by an amine, to prepare a compound of formula (IV). As used herein, an "amine" refers to a compound containing a nitrogen atom with a lone pair. In certain embodiments, the amine may be a primary amine, wherein the amine has two hydrogens and $R_1$ bound to the nitrogen. In certain embodiments, the amine may be a secondary amine, wherein the amine has one hydrogen and $R_1$ and $R_2$ bound to the nitrogen. In certain embodiments, the amine may be a tertiary amine, wherein the amine has $R_1$, $R_2$, and $R_3$ bound to the nitrogen. In certain embodiments, wherein the amine is a primary, secondary, or tertiary amine, $R_1$, $R_2$, and $R_3$ are each independently selected from one or a combination of deuterium, halo, amino, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, heterocyclyl, and —$S(O)_nR^9$ (n=0 to 2, $R^9$ is directly connected to S), wherein $R^9$ is selected from the group consisting of hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, and heterocyclyl. In certain embodiments, the amine is a cyclic amine, wherein the amine is a member of the ring and is either a secondary or a tertiary amine, such as piperidine, aziridine, or morpholino. In certain embodiments, the amine is an aromatic amine, wherein the nitrogen atom is a member of the aromatic ring. In certain embodiments, the amine is a secondary amine wherein $R_1$ is methoxy and $R_2$ is methyl.

In certain embodiments, the amine is a hydroxylamine of formula $R_4ONR_5R_6$, where $R_4$, $R_5$, and $R_6$ are each independently selected from the group consisting of hydrogen, deuterium, halo, amino, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, heterocyclyl, or —$S(O)_nR^9$ (n=0 to 2, $R^9$ is directly connected to S), wherein $R^9$ is selected from the group consisting of hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, and heterocyclyl. In certain embodiments, $R_4$ is methoxy, $R_5$ is hydrogen, and $R_6$ is methyl. In certain embodiments, the hydroxylamine is a methylated hydroxylamine, N-Methoxymethanamine, having the formula $CH_3ONHCH_3$.

In certain embodiments, contacting the compound of formula (III) with a halogenating agent is at a temperature of about −10° C. to about 100° C. In certain embodiments, the contacting is at a temperature of about −5° C. to about 5° C., about −3° C. to about 3° C., about 10° C. to about 90° C., about 25° C. to about 80° C., about 45° C. to about 65° C., or about 15° C. to about 85° C. In certain embodiments, the contacting is at a temperature of about 0° C.

In certain embodiments, contacting the compound of formula (III) with a halogenating agent is in the presence of a solvent (s-b). In certain embodiments, the solvent (s-b) is selected from the group consisting of dichloromethane, dimethylformamide (N,N-dimethylformamide) (DMF), diethyl ether, chloroform, 1,4-dioxane, toluene, pentane, cyclopentane, hexane, and benzene. In certain embodiments, the solvent (s-b) is dichloromethane. In certain embodiments, the solvent (s-b) is a mixture of solvents comprising dichloromethane and dimethylformamide (DMF).

In certain embodiments, the solvent (s-b) used in the presence of contacting the compound of formula (III) with a halogenating agent is present from about 5 vol to about 15 vol, about 8 vol to about 12 vol, about 9 vol to about 11 vol. In certain embodiments, the solvent (s-b) is present in about 5 vol, about 6 vol, about 7 vol, about 8 vol, about 9 vol, about 10 vol, about 11 vol, or about 12 vol.

In certain embodiments, the halogenating agent is present in an amount of about 1 to about 5 equiv, from about 1.25 to about 4.5 equiv, from about 2 to about 3 equiv, or from about 1.5 equiv to about 2.5 equiv. In certain embodiments, the halogenating agent is present in an amount of about 1 equiv, about 1.25 equiv, about 2 equiv, about 2.25 equiv, about 3 equiv, about 3.25 equiv, about 3.5 equiv, or about 4 equiv.

In certain embodiments, contacting the compound of formula (III) with a halogenating agent is for a duration of about 0.5, about 1, about 2, about 3, about 4 hours, or more and/or up to about 6 hours, about 7 hours, about 8 hours, about 9 hours, about 10 hours, about 15 hours, about 20 hours, about 25 hours, about 30 hours, about 40 hours or more. In certain embodiments, the contacting is for a duration of about 2.25 hours.

In certain embodiments, the amine is present in an amount of about 0.5 to about 5 equiv. In certain embodiments, the amine is present in an amount of about 0.75 to about 4 equiv, about 1.0 equiv to about 2.0 equiv, about 2.0 equiv to about 3 equiv, or about 2.25 equiv to about 3.25 equiv. In certain embodiments, the methylated hydroxylamine is present in an amount of about 1.2 equiv, 1.3 equiv, 1.4 equiv, or about 1.5 equiv.

In certain embodiments, the contacting with an amine to prepare a compound of formula IV is in the presence of a solvent (s-c). In certain embodiments, the solvent (s-c) is selected from the group consisting of tetrahydrofuran, ethyl acetate, dichloromethane, ethanol, methanol, acetone, methyl ethyl ketone, isopropanol, n-propanol, acetonitrile, and dimethyl sulfoxide. In certain embodiments, the solvent (s-c) is tetrahydrofuran.

In certain embodiments, the solvent (s-c) used in the presence of contacting with an amine to prepare a compound of formula IV is present from about 5 vol to about 15 vol, about 8 vol to about 12 vol, about 9 vol to about 11 vol. In certain embodiments, the solvent (s-c) is present in about 5 vol, about 6 vol, about 7 vol, about 8 vol, about 9 vol, about 10 vol, about 11 vol, or about 12 vol.

In certain embodiments, the contacting with an amine to prepare a compound of formula IV is in the presence of a base (b-c). In certain embodiments, the base (b-c) is selected from the group consisting of 1,8-diazabicyclo[5.4.0]undec-7-ene (DBU), NaHCO$_3$, Na$_2$CO$_3$, triethylamine (TEA), potassium tert-butoxide, sodium tert-butoxide, pyridine, potassium carbonate, sodium hydroxide, sodium hydride, potassium hydride, N,N-diisopropylethylamine (DIPEA), phosphazene bases, such as t-Bu-P$_4$, lithium diisopropylamide (LDA), silicon-based amides, such as sodium and potassium bis(trimethylsilyl)amide (NaHMDS and KHMDS, respectively), lithium tetramethylpiperidide (LiTMP), and 2,6-di-tert-butylpyridine. In certain embodiments, the base (b-c) is selected from the group consisting of diisopropylethylamine, pyridine, triethylamine, and 2,6-di-tert-butylpyridine. In certain embodiments, the base (b-c) is diisopropylethylamine.

In certain embodiments, the base (b-c) is present in an amount of about 1 equiv to about 5 equiv, about 2 equiv to about 3 equiv, or about 3 equiv to about 4 equiv. In certain embodiments, the base is present in about 2 equiv, about 2.25 equiv, or about 3.5 equiv.

In certain embodiments, the contacting with an amine to prepare a compound of formula (IV) is for a duration of about 0.5, about 1, about 2, about 3, about 4 hours, or more and/or up to about 6 hours, about 7 hours, about 8 hours, about 9 hours, about 10 hours, about 15 hours, about 20 hours, about 25 hours, about 30 hours, about 40 hours or more In certain embodiments, the contacting with an amine to prepare a compound of formula (IV) is at a temperature of about 0° C. to about 100° C. In certain embodiments, the contacting is at a temperature of about 10° C. to about 80° C., about 20° C. to about 60° C., or about 30° C. to about 50° C. In certain embodiments, the contacting is at a temperature of about 25° C.

In certain embodiments, the process described herein to prepare a compound of formula (IV) is capable of reaching a percent yield of formula (IV) of at least about 10%, about 20%, about 30%, about 40%, about 50%, about 60%, about 70%, about 80%, or about 90% and/or up to about 90%, about 91%, about 94%, or about 95%.

In certain embodiments, the process produces the compound of Formula (IV) having a purity above about 92%, above about 93%, above about 94%, above about 95%, above about 96%, above about 97%, above about 98% or above about 99%.

In certain embodiments, the compound of formula (IV) is not isolated.

In another aspect, the subject matter described herein is directed to processes for preparing a compound of formula (VI), the process comprising contacting a compound of formula (IV) with a compound of formula (V) in the presence of a base (b-d) and a solvent (s-d) to prepare a compound of formula (VI);

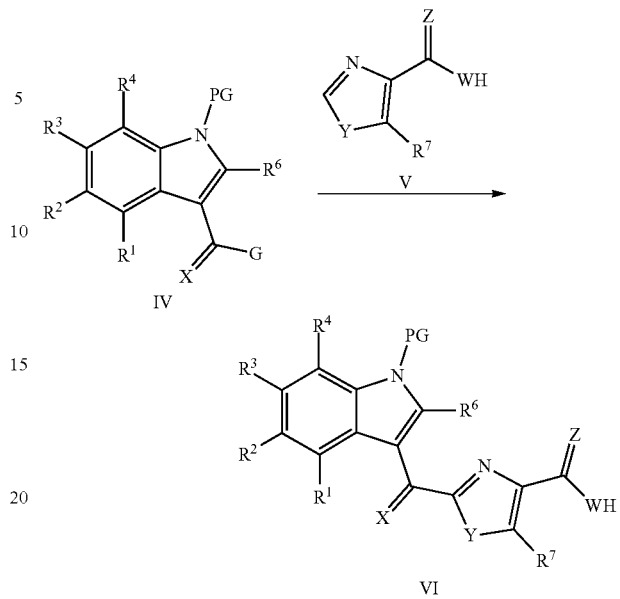

In certain embodiments, the base (b-d) used in the presence of contacting a compound of formula (IV) with a compound of formula (V) is selected from the group consisting of 1,8-diazabicyclo[5.4.0]undec-7-ene (DBU), NaHCO$_3$, Na$_2$CO$_3$, triethylamine (TEA), potassium tert-butoxide, sodium tert-butoxide, pyridine, potassium carbonate, sodium hydroxide, sodium hydride, potassium hydride, N,N-diisopropylethylamine (DIPEA), phosphazene bases, such as t-Bu-P4, lithium diisopropylamide (LDA), silicon-based amides, such as sodium, lithium, and potassium bis(trimethylsilyl)amide (NaHMDS, LiHMDS, and KHMDS, respectively), lithium tetramethylpiperidide (LiTMP), and 2,6-di-tert-butylpyridinepotassium. In certain embodiments, the base is selected from the group consisting of bis(trimethylsilyl)amide, lithium diisopropylamide, sodium bis(trimethylsilyl)amide, sodium tert-butoxide, and potassium tert-butoxide. In certain embodiments, the base is potassium bis(trimethylsilyl)amide.

In certain embodiments, the compound of formula (V) is contacted with a protecting group prior to being contacted with the compound of formula (IV). In certain embodiments, the protecting group is selected from the group consisting of allyl carbamate (Alloc), t-butyl carbamate (BOC), 9-fluorenylmethyl carbamate (FMOC), benzyl carbamate (Cbz), acetamide, chloroacetamide, trifluoroacetamide (TFA), phthalimide, benzylamine, triphenylmethylamine (tritylamine), benzylideneamine, p-toluenesulfonamide, and tosylamide.

In certain embodiments, the base used in the presence of the contacting a compound of formula (IV) (b-d) with a compound of formula (V) is present in an amount of about 1 equiv to about 5 equiv, about 2 equiv to about 3 equiv, or about 3 equiv to about 4 equiv. In certain embodiments, the base (b-d) is present in about 2 equiv, about 2.1 equiv, about 2.2 equiv, about 2.25 equiv, or about 3.5 equiv.

In certain embodiments, the solvent (s-d) used in the presence of contacting a compound of formula (IV) with a compound of formula (V) is selected from the group consisting of tetrahydrofuran, ethyl acetate, dichloromethane, ethanol, methanol, acetone, methyl ethyl ketone, isopropanol, n-propanol, acetonitrile, and dimethyl sulfoxide. In certain embodiments, the solvent (s-d) is tetrahydrofuran.

In certain embodiments, the compound of formula (V) is present in amount of about 0.25 equiv to about 5 equiv relative to 1 equiv of the compound of formula (IV). In certain embodiments, the compound of formula (V) is present in amount of about 0.5 equiv to about 4 equiv, about 1 equiv to about 3 equiv, about 1.25 equiv to about 2.25 equiv, or about 0.5 equiv to about 1.5 equiv relative to 1 equiv of the compound of formula (IV). In certain embodiments, the compound of formula (V) is present in amount of about 0.75 equiv, about 1 equiv, about 1.1 equiv, or about 1.2 equiv relative to 1 equiv of the compound of formula (IV).

In certain embodiments, contacting the compound of formula (IV) with a compound of formula (V) in the presence of a base (b-d) and a solvent (s-d) is at a temperature of about −10° C. to about 10° C. In certain embodiments, the contacting is at a temperature of about −5° C. to about 5° C., about −3° C. to about 3° C. In certain embodiments, the contacting is at a temperature of about 0° C.

In certain embodiments, contacting the compound of formula (IV) with a compound of formula (V) in the presence of a base (b-d) and a solvent (s-d) is for a duration of about 1 minute, about 2 minutes, about 3 minutes, about 4 minutes, about 5 minutes, about 6 minutes, about 7 minutes, about 8 minutes, about 9 minutes, about 10 minutes, about 15 minutes, about 25 minutes, about 0.5, about 1, about 2, about 3, about 4 hours, about 5 hours, about 6 hours, about 7 hours, about 8 hours, about 9 hours, about 10 hours, about 15 hours, about 20 hours, about 25 hours, about 30 hours, about 40 hours or more.

In certain embodiments, the compound of formula (VI) is not isolated.

In another aspect, the subject matter described herein is directed to processes for preparing a compound of formula I, the process comprising contacting a compound of formula (VI) with an acid.

In certain embodiments, the acid is selected from the group consisting of hydrochloric acid, sulfuric acid, trifluoroacetic acid, or nitric acid. In certain embodiments, the acid is hydrochloric acid (HCl). In certain embodiments, the acid is 1 M aqueous HCl.

In certain embodiments, wherein after the contacting of Formula IV with an acid, a solvent (s-e) is added. In certain embodiments, the solvent (s-e) is selected from the group consisting of water, methanol, ethanol, acetic acid, n-propanol, dichloromethane, and t-butanol. In certain embodiments, the solvent (s-e) is methanol. In certain embodiments, the solvent (s-e) is dichloromethane.

In certain embodiments, the compound of formula (I) is generated in a percent yield of at least about 5%, about 6%, about 7%, about 8%, about 9%, about 10%, about 11%, about 20%, about 30%, about 40%, about 50%, about 60%, about 70%, about 80%, or about 90% and/or up to about 90%, about 91%, about 94%, or about 95%.

In certain embodiments of the processes described above, the compounds of formulae (I), (II), (III), (IV), (V), and (VI) have W, X, Y, and Z as each independently O or S. In certain embodiments of the processes described above, X, Z, and W are each O and Y is S.

In certain embodiments of the processes described above, $R^1$, $R^2$, $R^3$, $R^4$, $R^5$, $R^6$, $R^7$, and $R^8$ are each independently selected from the group consisting of hydrogen, $C_1$-$C_6$ alkyl, halo, $C_1$-$C_6$ haloalkyl, and alkoxy. In certain embodiments, $R^1$, $R^2$, $R^3$, $R^4$, $R^5$, $R^6$, $R^7$, and $R^8$ are each independently selected from the group consisting of hydrogen, methyl, ethyl, and propyl. In certain embodiments, $R^1$, $R^2$, $R^3$, $R^4$, $R^5$, $R^6$, $R^7$, and $R^8$ are each independently selected from the group consisting of hydrogen and methyl.

In certain embodiments, in the compound of formula (II), $R^1$, $R^2$, $R^3$, $R^4$, $R^5$, $R^6$ are each hydrogen and X is O. In certain embodiments, in the compound of formula (III), $R^1$, $R^2$, $R^3$, $R^4$, and $R^6$ are each hydrogen, X is O, and PG is (BOC). In certain embodiments, in the compound of formula (IV), $R^1$, $R^2$, $R^3$, $R^4$, and $R^6$ are each hydrogen, X is O, and PG is (BOC). In certain embodiments, in the compound of formula (V), $R^7$ is hydrogen, Y is S, Z is O, and W is O. In certain embodiments, in the compound of formula (VI), $R^1$, $R^2$, $R^3$, $R^4$, $R^6$, and $R^7$ are each hydrogen, PG is (BOC), X is O, Y is S, Z is O, and W is O.

In certain embodiments, $R^1$, $R^2$, $R^3$, $R^4$, $R^5$, $R^6$, and $R^7$ are each hydrogen, $R^8$ is methyl, X is O, Y is S, Z is O, and W is O. In certain embodiments of the processes described above, the compound of Formula I is a compound having a structure:

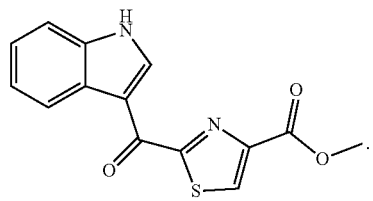 [SMILES: COC(=O)c1csc(C(=O)c2c[nH]c3ccccc23)n1]

In certain embodiments, the compound of Formula I has a purity above about 91% by HPLC. In certain embodiments, the compound of Formula I has a purity above about 92% by HPLC. In certain embodiments, the compound of Formula I has a purity above about 93% by HPLC. In certain embodiments, the compound of Formula I has a purity of about 93% to about 99% by HPLC. In certain embodiments, the purity is above about 95% by HPLC.

In certain embodiments of the processes described above, the compound of formula (III) is a compound having a structure:

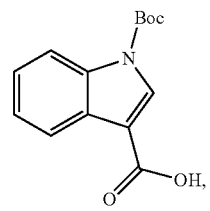 [SMILES: CC(C)(C)OC(=O)n1cc(C(=O)O)c2ccccc21]

wherein the compound has a purity above about 93% by HPLC. In certain embodiments, the compound of formula (III) is obtained in at least about 50% yield. In certain embodiments, the compound of formula (III) is obtained in about 57%, about 58%, about 59%, about 60%, about 70%, about 75%, about 76%, about 77%, about 78%, or about 79% yield.

In certain embodiments of the processes described above, in the compound of formula (IV), G is

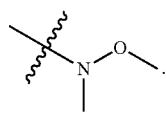 [SMILES: *N(C)OC]

In certain embodiments of the processes described above, the compound of formula (IV) is a compound having a structure:

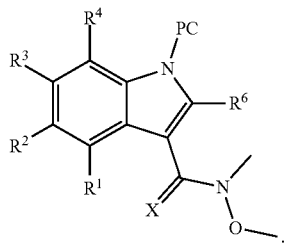

In certain embodiments of the processes described above, the compound of formula (IV) is a compound having a structure:

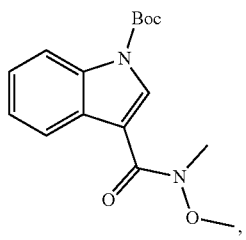 [SMILES: CON(C)C(=O)c1cn(C(=O)OC(C)(C)C)c2ccccc12]

wherein the compound has a purity above about 94% by HPLC. In certain embodiments, the compound of formula (IV) is obtained in at least about 90%, at least about 92%, at least about 93%, at least about 94%, or at least about 95% yield.

In certain embodiments, the methods described herein are directed to preparing ITE (1) in high yield with high purity. Scheme 1-1 depicts an overview for such a synthesis.

Scheme 1-1

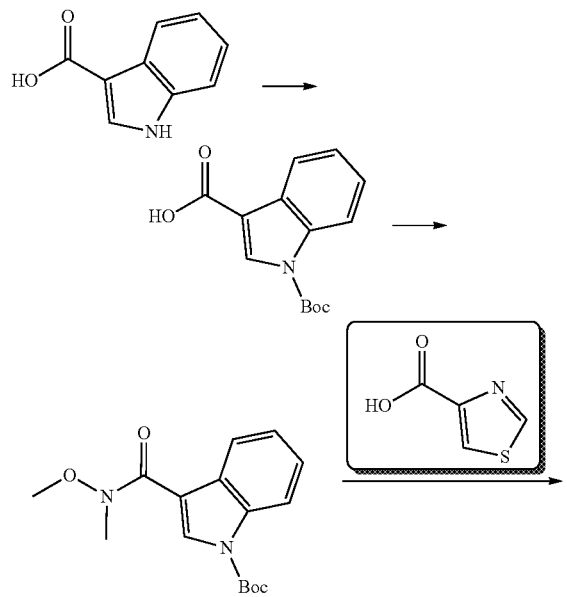

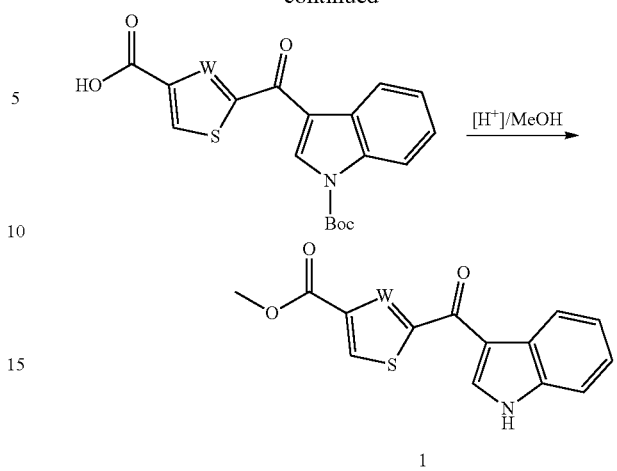

In certain embodiments, the methods described herein are directed to preparing 1-(tert-Butoxycarbonyl)-1H-indole-3-carboxylic acid in high yield, with high purity, from indole-3-carboxylic acid. Scheme 1-2 depicts an exemplary route for such a synthesis.

Scheme 1-2

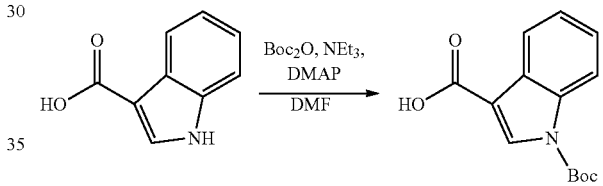

In certain embodiments, the methods described herein are directed to preparing tert-Butyl 3-(methoxy(methyl)carbamoyl)-1H-indole-1-carboxylate. Scheme 1-3 depicts an exemplary route for such a synthesis.

Scheme 1-3

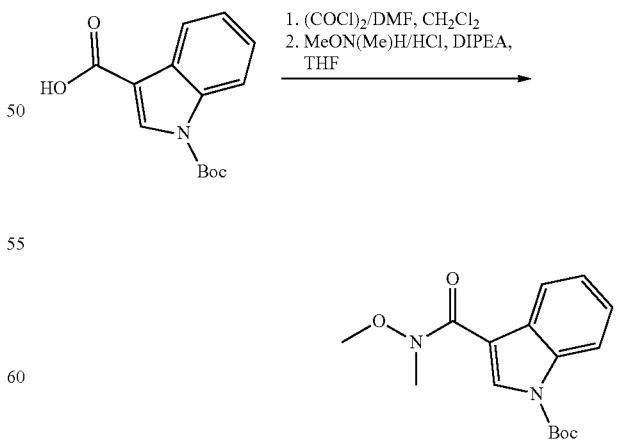

In certain embodiments, the methods described herein are directed to ITE. Scheme 1-4 depicts an exemplary route for such a synthesis.

Scheme 1-4

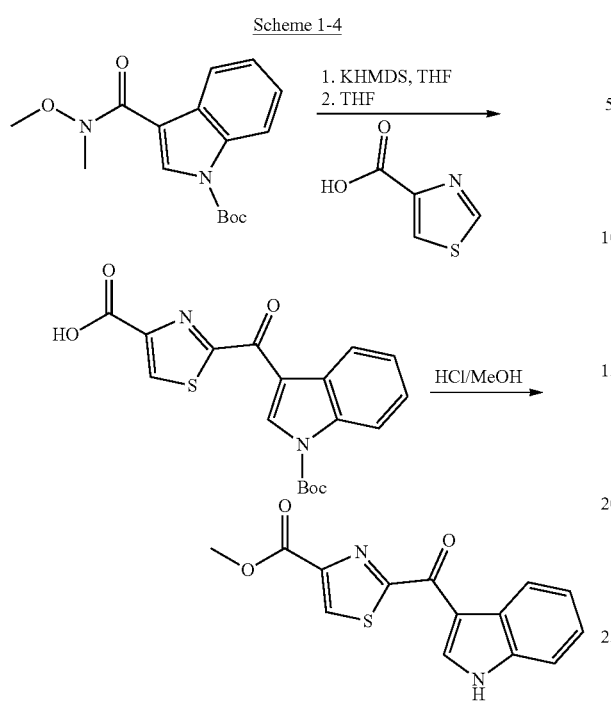

The subject matter described herein includes the following embodiments:

1. A process for the preparation of a compound of Formula I:

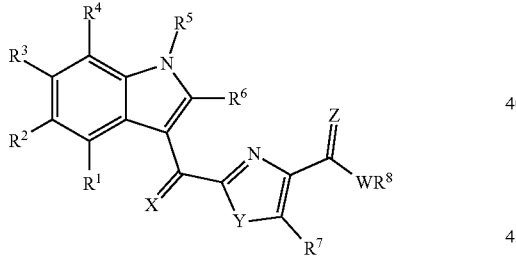

wherein W, X, Y, and Z are each independently selected from the group consisting of O, S, and NH;

$R^1$, $R^2$, $R^3$, $R^4$, $R^5$, $R^6$, $R^7$, and $R^8$ are each independently selected from the group consisting of hydrogen, deuterium, halo, amino, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, heterocyclyl, and —S(O)$_n$R$^9$(n=0 to 2, R$^9$ is directly connected to S), wherein $R^9$ is selected from the group consisting of hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, and heterocyclyl;

the process comprising:

contacting a compound of formula (II) with a protecting group in the presence of a nucleophile to prepare a compound of formula (III);

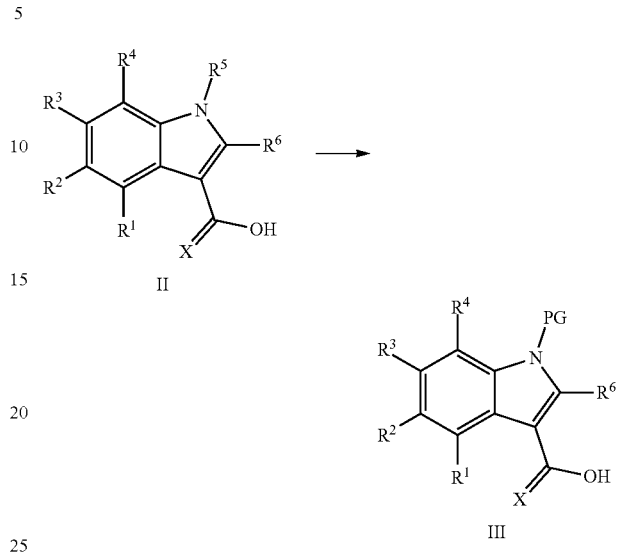

where PG is a protecting group;

contacting the compound of formula (III) with a halogenating agent, followed by an amine to prepare a compound of formula (IV);

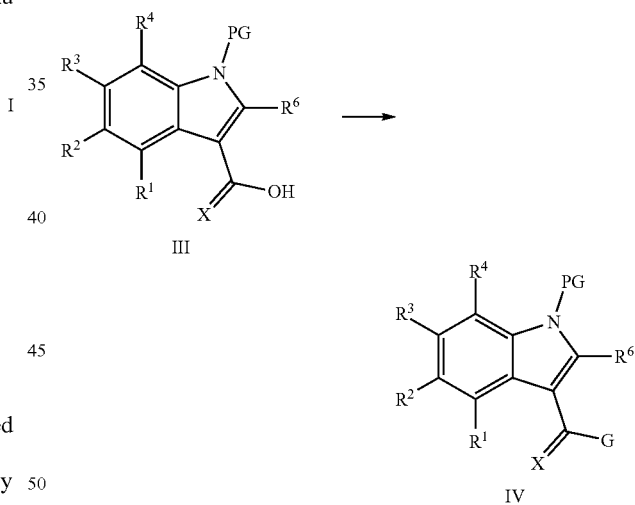

where G is selected from the group consisting of

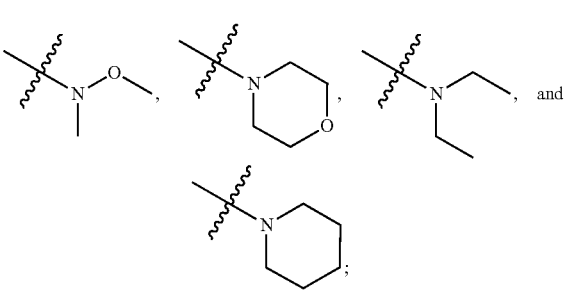

contacting the compound of formula (IV) with a compound of formula (V) in the presence of a base and a solvent to prepare a compound of formula (VI); and

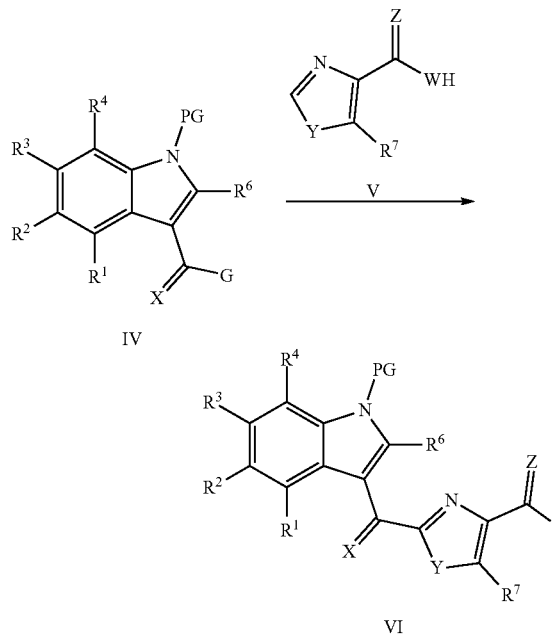

contacting the compound of formula (VI) with an acid; wherein, the compound of Formula I is prepared.
2. The process of embodiment 1, wherein said protecting group (PG) is selected from the group consisting of allyl carbamate (Alloc), t-butyl carbamate (BOC), 9-fluorenylmethyl carbamate (FMOC), benzyl carbamate (Cbz), acetamide, chloroacetamide, trifluoroacetamide (TFA), phthalimide, benzylamine, triphenylmethylamine (tritylamine), benzylideneamine, p-toluenesulfonamide, and tosylamide.
3. The process of embodiment 1 or 2, wherein said protecting group is t-butyl carbamate (BOC).
4. The process of any one of embodiments 1-3, wherein said nucleophile is selected from the group consisting of 1,4-Diazabicyclo[2.2.2]octane (DABCO), quinuclidine, N-Methylpiperidine, N-methylmorpholine, and 4-dimethylaminopyridine (DMAP).
5. The process of any one of embodiments 1-4, wherein said nucleophile is 4-dimethylaminopyridine (DMAP).

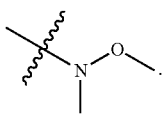 [SMILES: *N(C)OC]

6. The process of any one of embodiments 1-5, wherein G is
7. The process of any one of embodiments 1-6, wherein the protecting group is present in an amount from about 1 to about 5 equivalents.
8. The process of any one of embodiments 1-7, wherein the nucleophile is present in an amount from about 0.05 to about 2 equivalents.
9. The process of any one of embodiments 1-8, wherein prior to said contacting the compound of formula (II) with a protecting group in the presence of a nucleophile, said compound of formula (II) is contacted with a solvent (s-a) and a base (b-a) to form a mixture.
10. The process of any one of embodiments 1-9, wherein said solvent (s-a) is selected from the group consisting of ethyl acetate, DMF, DMSO, dichloromethane, toluene, isopropyl acetate, acetonitrile, and acetone.
11. The process of any one of embodiments 1-10, wherein said solvent (s-a) is DMF.
12. The process of any one of embodiments 1-11, wherein said base (b-a) is selected from the group consisting of diisopropylethylamine, pyridine, triethylamine, and 2,6-di-tert-butylpyridine.
13. The process of any one of embodiments 1-12, wherein said base (b-a) is triethylamine.
14. The process of any one of embodiments 1-13, wherein said solvent (s-a) is present in an amount from about 2 vol to about 7 vol.
15. The process of any one of embodiments 1-14, wherein said base (b-a) is present in an amount from about 1 to about 5 equivalents.
16. The process of any one of embodiments 1-15, wherein said halogenating agent is a chlorination agent.
17. The process of any one of embodiments 1-16, wherein said chlorination agent is selected from the group consisting of $SOCl_2$, $(COCl)_2$, and $POCl_3$.
18. The process of any one of embodiments 1-17, wherein said chlorination agent is $(COCl)_2$.
19. The process of any one of embodiments 1-18, wherein said amine is a hydroxylamine.
20. The process of any one of embodiments 1-19, wherein said hydroxylamine is N-Methoxymethanamine.
21. The process of any one of embodiments 1-20, wherein said contacting the compound of formula (III) with a halogenating agent is at a temperature of about −5° C. to about 5° C.
22. The process of any one of embodiments 1-21, wherein said contacting the compound of formula (III) with a halogenating agent is in the presence of a solvent (s-b).
23. The process of any one of embodiments 1-22, wherein the solvent (s-b) is selected from the group consisting of dichloromethane, diethyl ether, chloroform, 1,4-dioxane, toluene, pentane, cyclopentane, hexane, and benzene.
24. The process of any one of embodiments 1-23, wherein said solvent (s-b) is dichloromethane.
25. The process of any one of embodiments 1-24, wherein said solvent (s-b) is present from about 8 vol to about 12 vol.
26. The process of any one of embodiments 1-25, wherein said halogenating agent is present in an amount of about 1.5 equiv to about 2.5 equiv.
27. The process of any one of embodiments 1-26, wherein said amine is present in an amount of about 1.0 equiv to about 2.0 equiv.
28. The process of any one of embodiments 1-27, wherein said contacting with an amine to prepare a compound of formula IV is in the presence of a solvent (s-c) and a base (b-c).
29. The process of any one of embodiments 1-28, wherein said solvent (s-c) is selected from the group consisting of tetrahydrofuran, ethyl acetate, dichloromethane, ethanol, methanol, acetone, methyl ethyl ketone, isopropanol, n-propanol, acetonitrile, and dimethyl sulfoxide.
30. The process of any one of embodiments 1-29, wherein said solvent (s-c) is tetrahydrofuran.

31. The process of any one of embodiments 1-30, wherein said base (b-c) is selected from the group consisting of diisopropylethylamine, pyridine, triethylamine, and 2,6-di-tert-butylpyridine.
32. The process of any one of embodiments 1-31, wherein said base (b-c) is diisopropylethylamine.
33. The process of any one of embodiments 1-32, wherein said solvent (s-c) is present from about 8 vol to about 12 vol.
34. The process of any one of embodiments 1-33, wherein said base (b-c) is present in an amount of about 2 equiv to about 3 equiv.
35. The process of any one of embodiments 1-34, wherein said base (b-d) is selected from the group consisting of potassium bis(trimethylsilyl)amide, lithium bis(trimethylsilyl)amide, lithium diisopropylamide, sodium bis(trimethylsilyl)amide, sodium tert-butoxide, and potassium tert-butoxide.
36. The process of any one of embodiments 1-35, wherein said base (b-d) is potassium bis(trimethylsilyl)amide.
37. The process of any one of embodiments 1-36, wherein said solvent (s-d) is selected from the group consisting of tetrahydrofuran, ethyl acetate, dichloromethane, ethanol, methanol, acetone, methyl ethyl ketone, isopropanol, n-propanol, acetonitrile, and dimethyl sulfoxide.
38. The process of any one of embodiments 1-37, wherein said solvent (s-d) is tetrahydrofuran.
39. The process of any one of embodiments 1-38, wherein said acid is selected from the group consisting of hydrochloric acid, sulfuric acid, and nitric acid.
40. The process of any one of embodiments 1-39, wherein said acid is hydrochloric acid.
41. The process of any one of embodiments 1-40, wherein after the contacting of Formula IV with an acid, a solvent (s-e) is added.
42. The process of any one of embodiments 1-41, wherein said solvent (s-e) is selected from the group consisting of water, methanol, ethanol, acetic acid, n-propanol, and t-butanol.
43. The process of any one of embodiments 1-42, wherein said solvent (s-e) is methanol.
44. The process of any one of embodiments 1-43, wherein the compound of formula (V) is present in amount of about 0.5 equiv to 1.5 equiv relative to 1 equiv of the compound of formula (IV).
45. The process of any one of embodiments 1-44, wherein contacting the compound of formula (IV) with a compound of formula (V) in the presence of a base (b-d) and a solvent (s-d) is at a temperature of about −5° C. to about 5° C.
46. The process of any one of embodiments 1-45, wherein said protecting group is t-butyl carbamate (BOC), said nucleophile is 4-dimethylaminopyridine (DMAP), said halogenating agent is (COCl)$_2$, said amine is N-Methoxymethanamine, said base (b-d) is potassium bis(trimethylsilyl)amide, said solvent (s-d) is tetrahydrofuran, and said acid is hydrochloric acid.
47. The process of any one of embodiments 1-46, wherein W, X, Y, and Z are each independently O or S.
48. The process of any one of embodiments 1-47, wherein X, Z, and W are each O and Y is S.
49. The process of any one of embodiments 1-48, wherein $R^1$, $R^2$, $R^3$, $R_4$, $R^5$, $R^6$, $R_7$, and $R^8$ are each independently selected from the group consisting of hydrogen, $C_1$-$C_6$ alkyl, halo, $C_1$-$C_6$ haloalkyl, and alkoxy.

50. The process of any one of embodiments 1-49, wherein $R^1$, $R^2$, $R^3$, $R_4$, $R^5$, $R^6$, $R_7$, and $R^8$ are each independently selected from the group consisting of hydrogen, methyl, ethyl, and propyl.
51. The process of any one of embodiments 1-50, wherein the compound of Formula I is a compound having a structure:

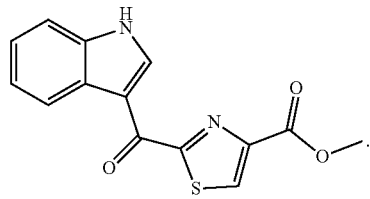 [SMILES: COC(=O)c1csc(C(=O)c2c[nH]c3ccccc23)n1]

52. The process of any one of embodiments 1-51, wherein the compound of Formula I has a purity above about 93% by HPLC.
53. The process of any one of embodiments 1-52, wherein the purity of the compound of Formula I is about 93% to about 99% by HPLC.
54. The process of any one of embodiments 1-53, wherein the purity of the compound of Formula I is above about 95% by HPLC.
55. A process for the preparation of a compound of formula (III), comprising: contacting a compound of formula (II) with a protecting group in the presence of a nucleophile to prepare a compound of formula (III);

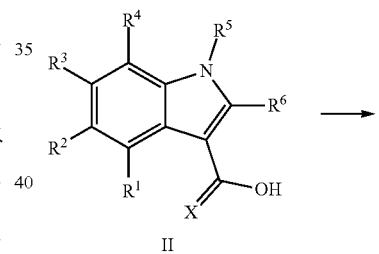

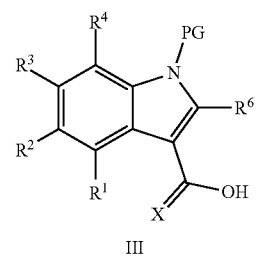

wherein PG is a protecting group selected from the group consisting of allyl carbamate (Alloc), t-butyl carbamate (BOC), 9-fluorenylmethyl carbamate (FMOC), benzyl carbamate (Cbz), acetamide, chloroacetamide, trifluoroacetamide (TFA), phthalimide, benzylamine, triphenylmethylamine (tritylamine), benzylideneamine, p-toluenesulfonamide, and tosylamide;

X is selected from the group consisting of O, S, and NH;

$R^1$, $R^2$, $R^3$, $R^4$, $R^5$, and $R^6$ are each independently selected from the group consisting of hydrogen, deuterium, halo, amino, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, heterocyclyl, and —S(O)$_n$R$^9$ (n=0 to 2, R$^9$ is directly connected to S), wherein R$^9$ is selected from the group consisting of hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, and heterocyclyl.

56. The process of embodiment 55, wherein the compound of formula (III) is a compound having a structure:

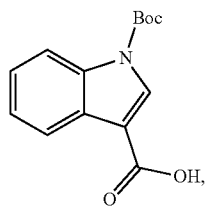 [SMILES: CC(C)(C)OC(=O)n1cc(C(=O)O)c2ccccc21]

wherein said compound has a purity above about 93% by HPLC.

57. The process of embodiment 55 or 56, wherein said compound is obtained in at least about 50% yield.

58. A process for the preparation of a compound of formula (IV), comprising contacting a compound of formula (III) with a halogenating agent, followed by an amine:

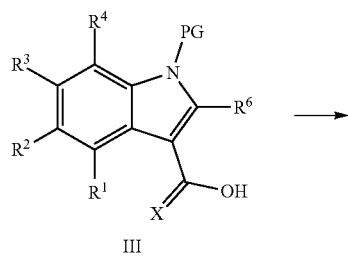

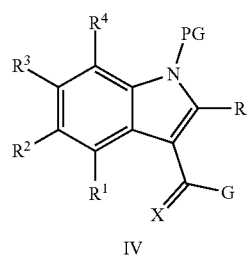

where G is selected from the group consisting of where G is selected from the group consisting of

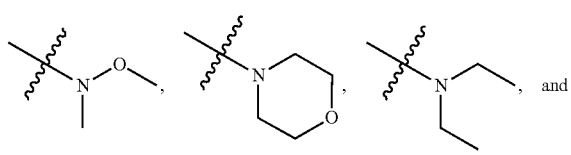

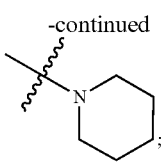

PG is a protecting group selected from the group consisting of allyl carbamate (Alloc), t-butyl carbamate (BOC), 9-fluorenylmethyl carbamate (FMOC), benzyl carbamate (Cbz), acetamide, chloroacetamide, trifluoroacetamide (TFA), phthalimide, benzylamine, triphenylmethylamine (tritylamine), benzylideneamine, p-toluenesulfonamide, and tosylamide;

X is selected from the group consisting of 0, S, and NH; and R', R$^2$, R$^3$, R$^4$, and R$^6$ are each independently selected from the group consisting of hydrogen, deuterium, halo, amino, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, heterocyclyl, and —S(O)$_n$R$^9$ (n=0 to 2, R$^9$ is directly connected to S), wherein R$^9$ is selected from the group consisting of hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, hal oc arb onyl oxy, carbonylthio, halocarbonylthio, thiocarbonyloxy, halothiocarbonyloxy, thiocarbonylthio, halothiocarbonylthio, aryl, heteroaryl, cycloalkyl, and heterocyclyl.

59. The process of embodiment 58, wherein said amine is a hydroxylamine.
60. The process of embodiment 58 or 59, wherein said hydroxylamine is N-Methoxymethanamine.
61. The process of any one of embodiments 58-60, wherein G is

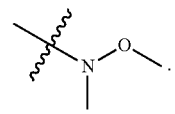 [SMILES: *N(C)OC]

62. The process of any one of embodiments 58-61, wherein the compound of formula (IV) is a compound having a structure:

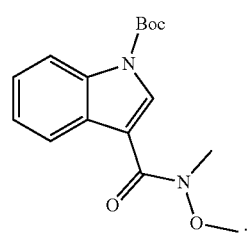 [SMILES: CON(C)C(=O)c1cn(C(=O)OC(C)(C)C)c2ccccc12]

63. A process for the preparation of a compound of formula (VI), comprising contacting a compound of formula (IV) with a compound of formula (V) in the presence of a base and a solvent:

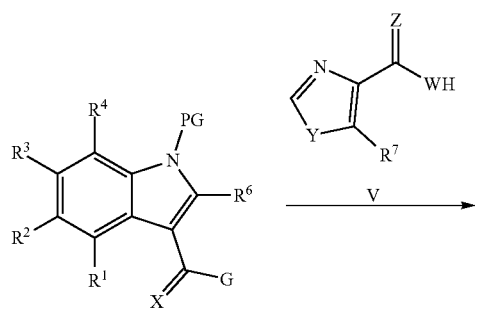

where G is selected from the group consisting of

PG is a protecting group selected from the group consisting of allyl carbamate (Alloc), t-butyl carbamate (BOC), 9-fluorenylmethyl carbamate (FMOC), benzyl carbamate (Cbz), acetamide, chloroacetamide, trifluoroacetamide (TFA), phthalimide, benzylamine, triphenylmethylamine (tritylamine), benzylideneamine, p-toluenesulfonamide, and tosylamide;

X, Y, and Z are independently selected from the group consisting of O, S, and NH; $R^1$, $R^2$, $R^3$, $R^4$, $R^6$, and $R^7$ are each independently selected from the group consisting of hydrogen, deuterium, halo, amino, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, heterocyclyl, and —S(O)$_n$R$^9$ (n=0 to 2, $R^9$ is directly connected to S), wherein $R^9$ is selected from the group consisting of hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, and heterocyclyl.

64. The process of embodiment 63, where G is

65. The process of embodiment 63 or 64, wherein the compound of formula (VI) is a compound having a structure:

66. A process for the preparation of a compound of Formula I:

wherein, W, X, Y, and Z are each independently selected from the group consisting of O, S, and NH;

$R^1$, $R^2$, $R^3$, $R^4$, $R^5$, $R^6$, $R^7$, and $R^8$ are each independently selected from the group consisting of hydrogen, deuterium, halo, amino, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, heterocyclyl, and —S(O)$_n$R$^9$(n=0 to 2, $R^9$ is directly connected to S), wherein $R^9$ is selected from the group consisting of hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, and heterocyclyl;

the process comprising: contacting a compound of formula (III) with a halogenating agent, followed by an amine to prepare a compound of formula IV, wherein PG is protecting group;

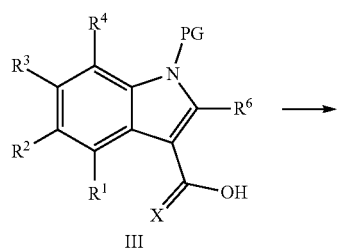

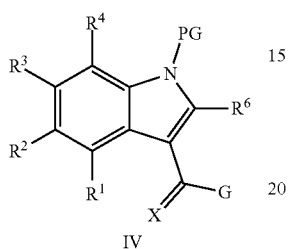

contacting the compound of formula (IV) with a compound of formula (V) in the presence of a base and a first solvent to prepare a compound of formula (VI);

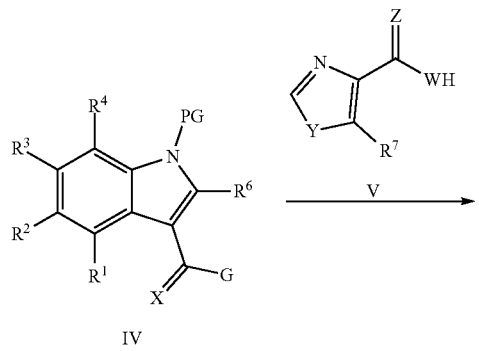

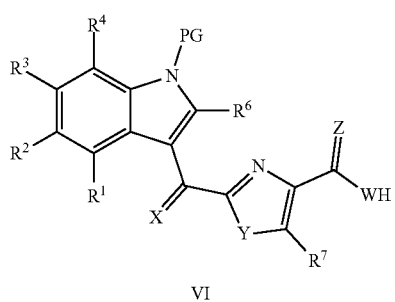

where G is selected from the group consisting of

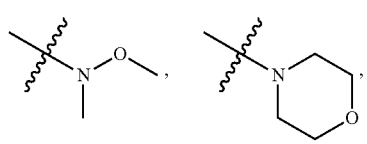

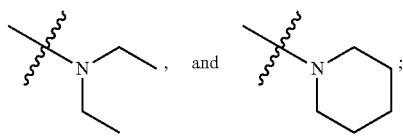

and contacting the compound of formula (VI) with an acid; wherein, the compound of Formula I is prepared.

67. The process of embodiment 66, where G is

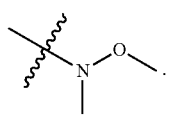 [SMILES: *N(C)OC]

The present invention is further described in the following non-limiting Examples. It should be understood that these Examples, while indicating preferred embodiments of the invention, are given by way of illustration only.

EXAMPLES

Methyl 2-(1H-indole-3-carbonyl)thiazole-4-carboxylate (ITE) (1) was prepared according to the present disclosure.

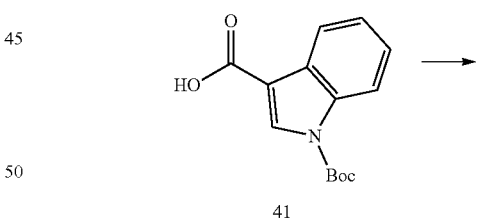

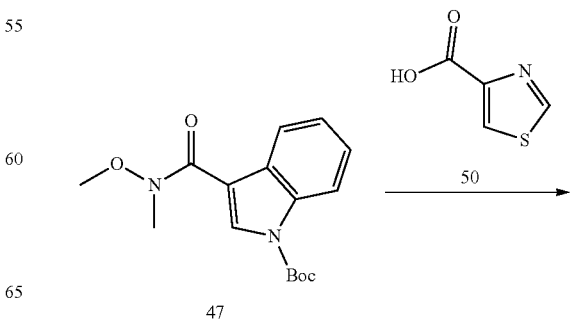

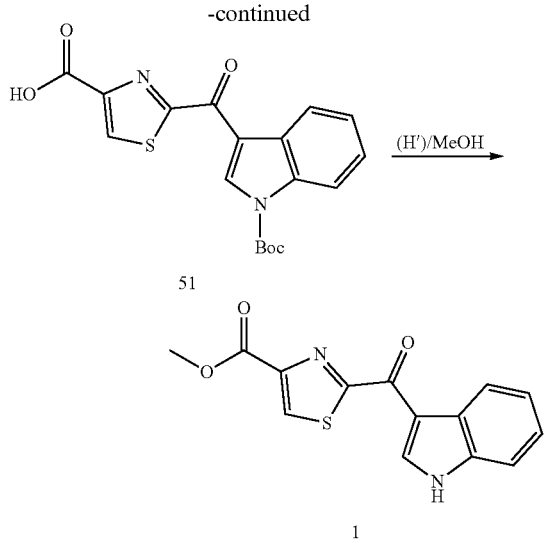

Example 1

Preparation of 1-(tert-Butoxycarbonyl)-1H-indole-3-carboxylic acid (41)

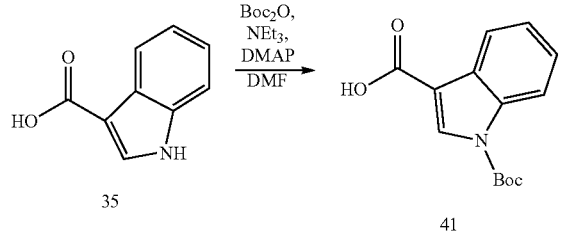

A solution of indole-3-carboxylic acid (35) (0.8 g, 5.0 mmol, 1 equiv) and DMAP (61 mg, 0.50 mmol, 0.1 equiv) in DMF (5 mL) was prepared and NEt₃ (2.1 mL, 14.9 mmol, 3 equiv) was added. Subsequently, a solution of Boc₂O (1.63 g, 7.5 mmol) in DMF (1 mL) was added and the obtained mixture was stirred at room temperature overnight. Satd. aqueous NaHCO₃ (2 mL) was added and the mixture was stirred for 1 h. The reaction mixture was mixed with 5% aqueous KHSO₄ (20 mL) and extracted with EtOAc (2×20 mL). Combined organic layers were washed with brine (10 mL), dried over Na₂SO₄, and concentrated by rotary evaporation. The crude material was triturated with MTBE/heptane (3:7), the solid was filtered and dried in vacuo yielding the title compound (41) as a yellow solid (1.0 g, 77% yield). HPLC (C₁₈) $t_R$=3.69 min. LCMS (ESI⁻, C₁₈) $t_R$=2.09 min, m/z=260.2 (calcd 260.1 for [M−H]⁻). ¹H NMR (400 MHz, CDCl₃) δ8.39 (s, 1H), 8.24-8.17 (m, 2H), 7.44-7.34 (m, 2H), 1.70 (s, 9H).

Example 2

Scaled-Up Preparation of 1-(tert-Butoxycarbonyl)-1H-indole-3-carboxylic acid (41)

To a solution of indole-3-carboxylic acid (35) (20 g, 124 mmol) in DMF (20 mL) was added NEt₃ (51.9 mL, 372 mmol). Then, a solution of Boc₂O (40.6 g, 186 mmol) in DMF (80 mL), and DMAP (1.52 g, 12.4 mmol) were added. The mixture was stirred at room temperature for 4.25 h. Following this, a second portion of Boc₂O (13.5 g, 62.1 mmol) was added, and the obtained mixture was stirred at room temperature for 22 h. Satd. aqueous NaHCO₃ (30 mL) was added and the obtained suspension was stirred for 1.25 h. To the reaction mixture was added EtOAc (250 mL) and 5% aqueous KHSO₄ (250 mL), the phases were separated, and the pH of the aqueous layer was adjusted to 3-4 with 6M aqueous HCl. The aqueous layer was extracted with EtOAc (2×200 mL), and the combined organic layers were washed with water (250 mL) and brine (100 mL) and were concentrated by rotary evaporation. Trituration with MTBE/heptane (1:1) yielded the title compound (41) as a yellow solid (19 g, 59% yield). HPLC (C₁₈) $t_R$=3.69 min. LCMS (ESI⁻, C₁₈) $t_R$=2.09 min, m/z=260.2 (calcd 260.1 for [M−H]⁻).

Example 3

Preparation of tert-Butyl 3-(methoxy(methyl)carbamoyl)-1H-indole-1-carboxylate

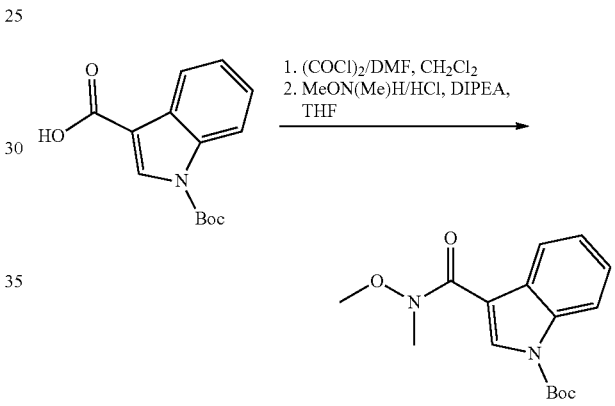

A suspension of 1-(tert-butoxycarbonyl)-1H-indole-3-carboxylic acid (6.1 g, 23.4 mmol) (41, from Example 2) in CH₂Cl₂ (61 mL, 10 vol) was cooled to 0° C. and a catalytic amount of DMF (0.1 mL, 6 mol %) was added. Oxalyl chloride (4.1 mL, 46.7 mmol, 2 equiv) was added dropwise and the obtained mixture was stirred at room temperature for 2.25 h. The white suspension was concentrated and dried in vacuo and the obtained crude acid chloride was directly used in the subsequent step. To the crude acid chloride was added MeON(Me)H.HCl (48) (2.96 g, 30.4 mmol, 1.3 equiv.) and THF (61 mL, 10 vol.) and with ice-cooling, DIPEA (10.2 mL, 58.4 mmol, 2.5 equiv.) was added. The obtained mixture was stirred at room temperature for 3 h. The reaction mixture was partitioned between MTBE (50 mL, 8.2 vol.) and 5% aqueous KHSO₄ (50 mL). The aqueous layer was separated, and the organic layer was washed with satd. aqueous NaHCO₃ (2×50 mL), and brine (20 mL). The organic layer was dried over Na₂SO₄, concentrated by rotary evaporation, and the residue was dried in vacuo (T=40° C.) to yield the title compound (47) as a white solid (6.71 g, 94% yield and 94% HPLC Purity). An HPLC chromatogram is provided in FIG. 1. HPLC (C₁₈) $t_R$=3.70 min. LCMS (ESI⁺, C₁₈): $t_R$=2.10 min, m/z=305.2 (calcd 305.2 for [M+H]⁺). ¹H NMR (400 MHz, DMSO-d₆) δ8.24 (s, 1H), 8.20 (d, J=8.5 Hz, 1H), 8.09 (d, J=8.4 Hz, 1H), 7.43-7.28 (m, 2H), 3.72 (s, 3H), 3.30 (s, 3H), 1.65 (s, 9H).

Example 4

Preparation of methyl 2-(1H-indole-3-carbonyl)thiazole-4-carboxylate (ITE) (1)

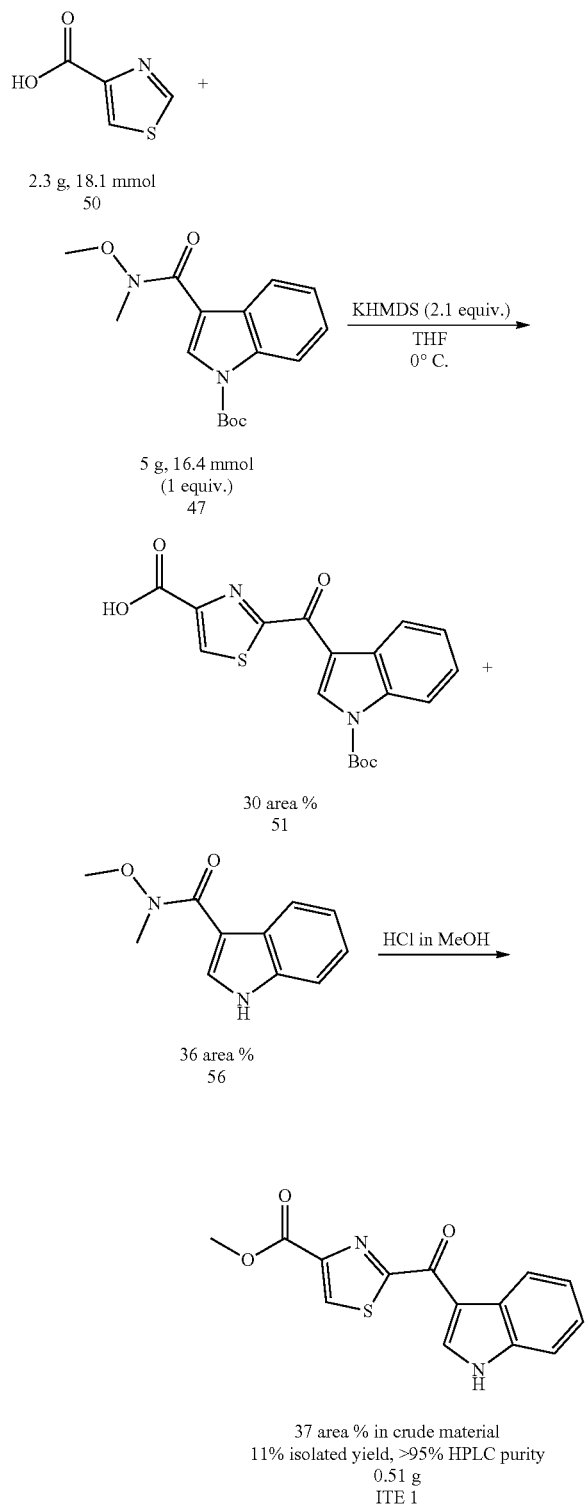

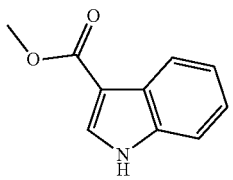

Figure 2:
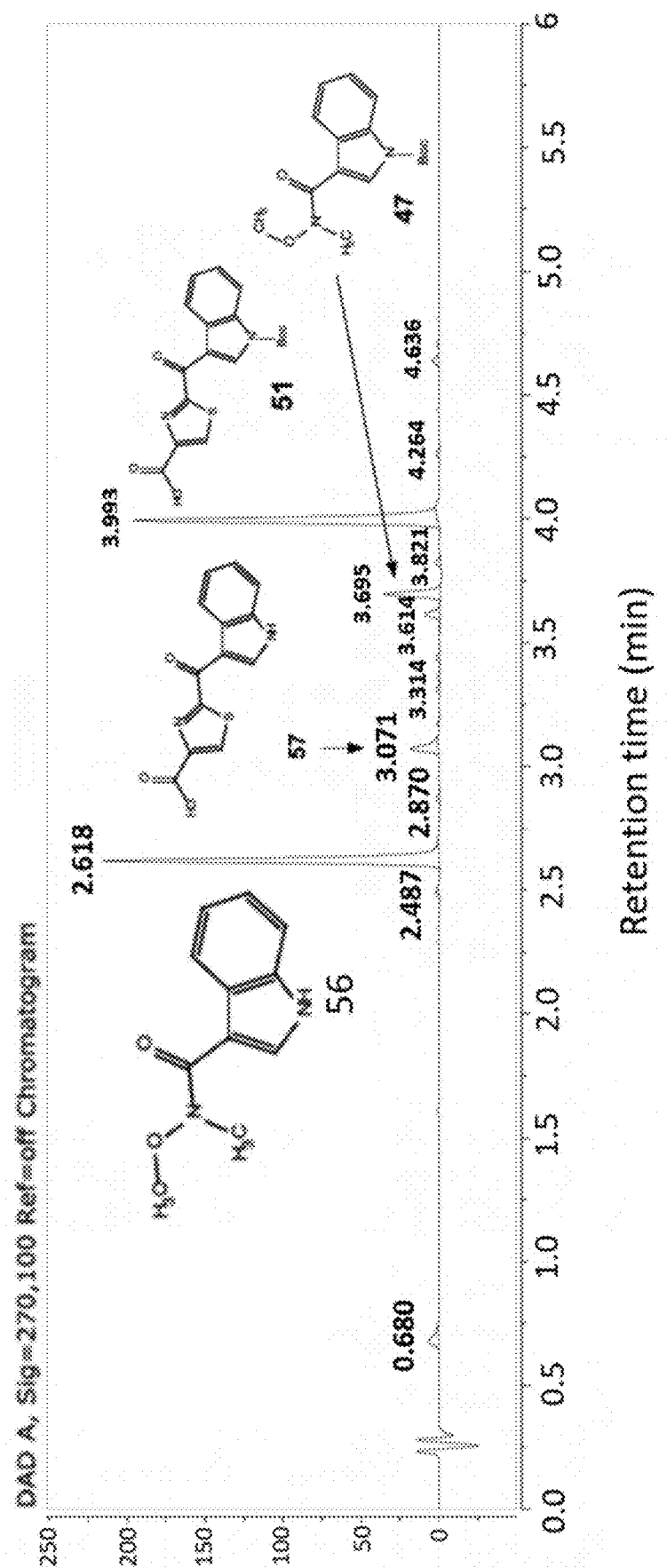
FIG. 2 shows an HPLC chromatogram 5 hours into the preparation of ITE, following the addition of thiazole-4-carboxylic acid (50) to the reaction mixture.
Figure 3:
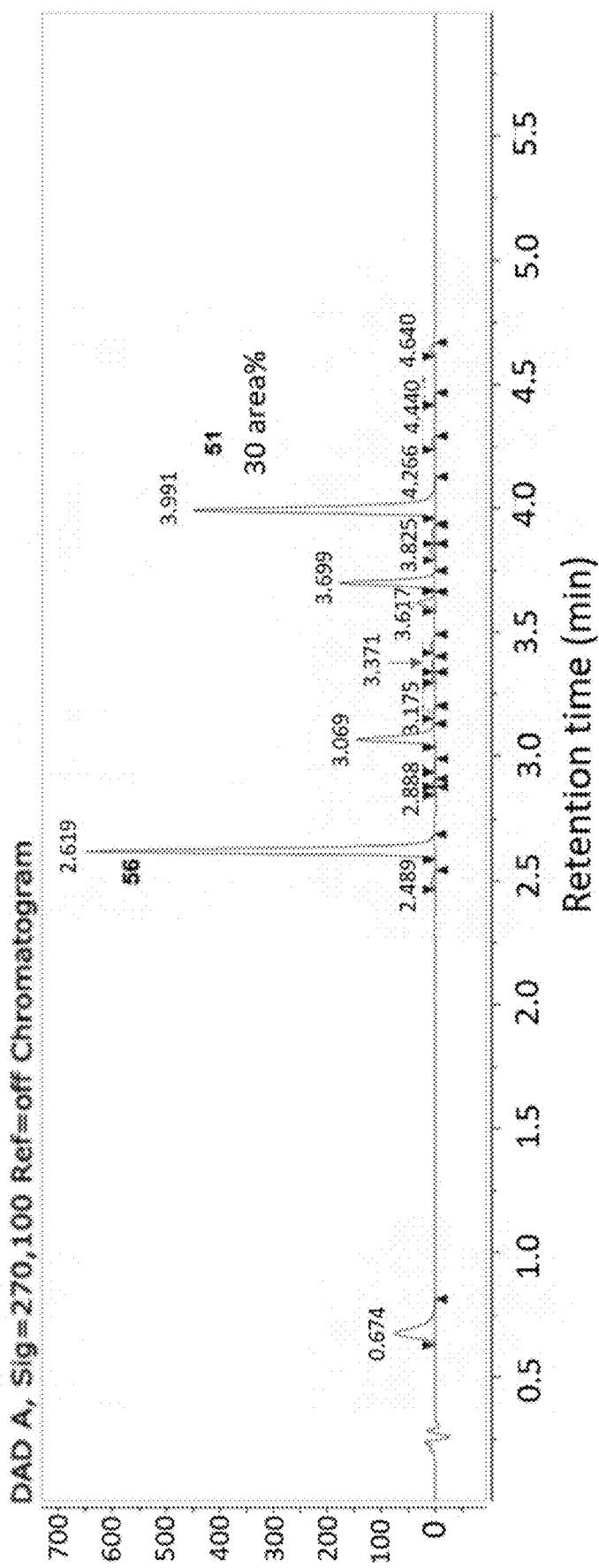
FIG. 3 shows an HPLC chromatogram of the intermediate (51).

A solution of tert-Butyl 3-(methoxy(methyl)carbamoyl)-1H-indole-1-carboxylate (47) (5 g, 16.4 mmol, 1 equiv.) in THF (30 mL) was cooled to 0° C. and KHMDS (41.1 mL, 36.1 mmol, 2.2 equiv. 20 wt % in THF) was added dropwise within 5 min. This resulted in an orange solution. A solution of thiazole-4-carboxylic acid (50) (2.3 g, 18.1 mmol, 1.1 equiv.) in THF (70 mL) was added dropwise in 30 min. The resulting brown mixture was stirred with ice-cooling for 7 h. HPLC analysis indicated an incomplete conversion of (47) (7 area % left), 40 area % of unprotected amide (56), and 42 area % of intermediate (51) after about 5 hours of stirring (FIG. 2). To the cold reaction was added 1M aqueous HCl (100 mL) and the resulting mixture was extracted with EtOAc (3×100 mL). Combined organic layers were washed with brine (100 mL), dried over $Na_2SO_4$, and concentrated by rotary evaporation. Approximately 7.1 g of a brown wax was obtained. An HPLC chromatogram is shown in FIG. 3.

The obtained crude material was used in the subsequent step without further purification. MeOH (20 mL) was cooled to 0° C. and $SOCl_2$ (6.0 mL, 82 mmol, 5 equiv. with respect to initially used 47) was added dropwise. To the solution was added a suspension of the previously obtained crude material in MeOH (40 mL), the cooling bath was removed, and the resulting mixture was warmed to 55° C. for 3 h, resulting in a dark brown solution. HPLC analysis indicated 42 area % of Boc unprotected methyl ester (58) and 36 area % of ITE (1).

Figure 4:
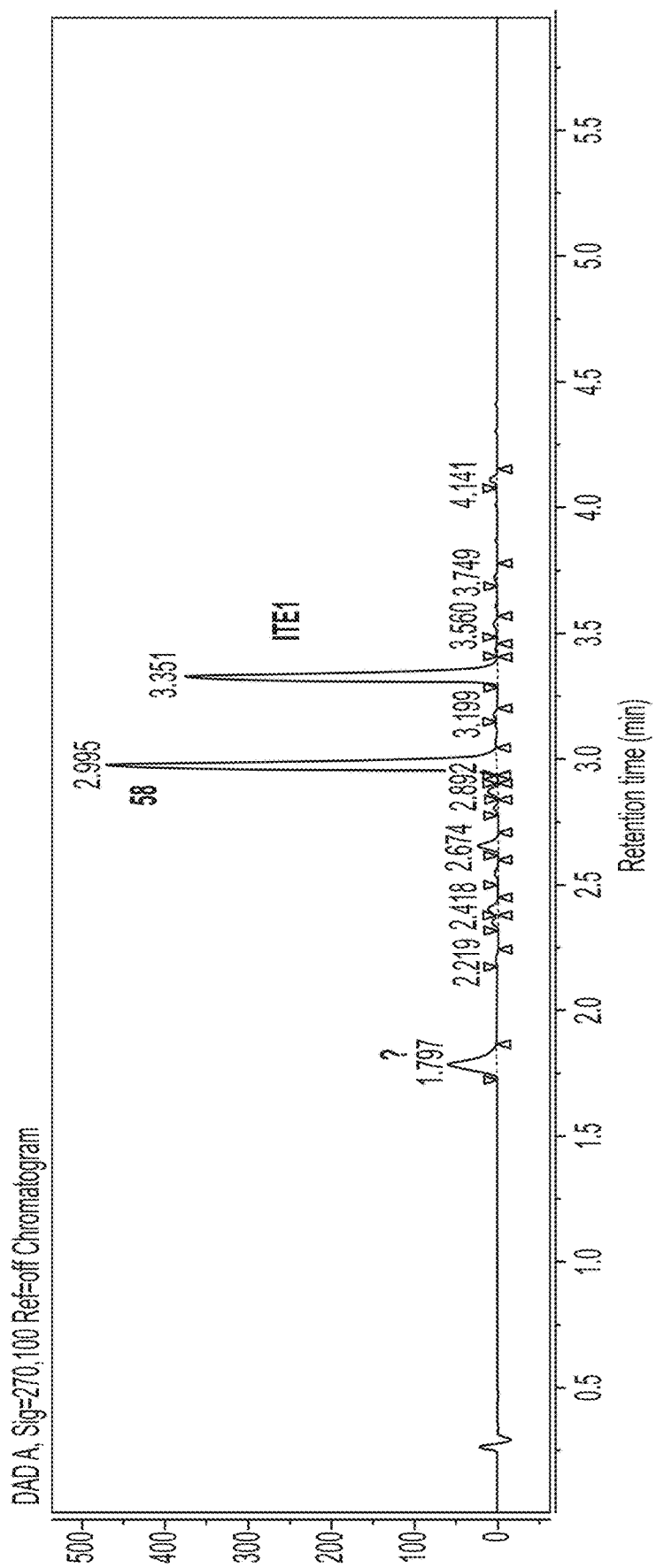
FIG. 4 shows an HPLC chromatogram of ITE (1) prior to purification.

The mixture was cooled to room temperature and was concentrated by rotary evaporation. The residue was mixed with 1M aqueous HCl (100 mL) and the resulting suspension was extracted with $CH_2Cl_2$ (3×100 mL). Combined organic layers were washed with satd. aqueous $NaHCO_3$ (100 mL), $H_2O$ (100 mL), and brine (50 mL), were dried over $Na_2SO_4$, and concentrated by rotary evaporation. About 4.7 g of crude product was obtained. This indicated that no product was lost during the workup procedure and that complete conversion of the indole starting material to ITE (1) occurred (100% of theory). HPLC analysis showed 37 area % of ITE (1) in the crude material (FIG. 4).

Figure 5:
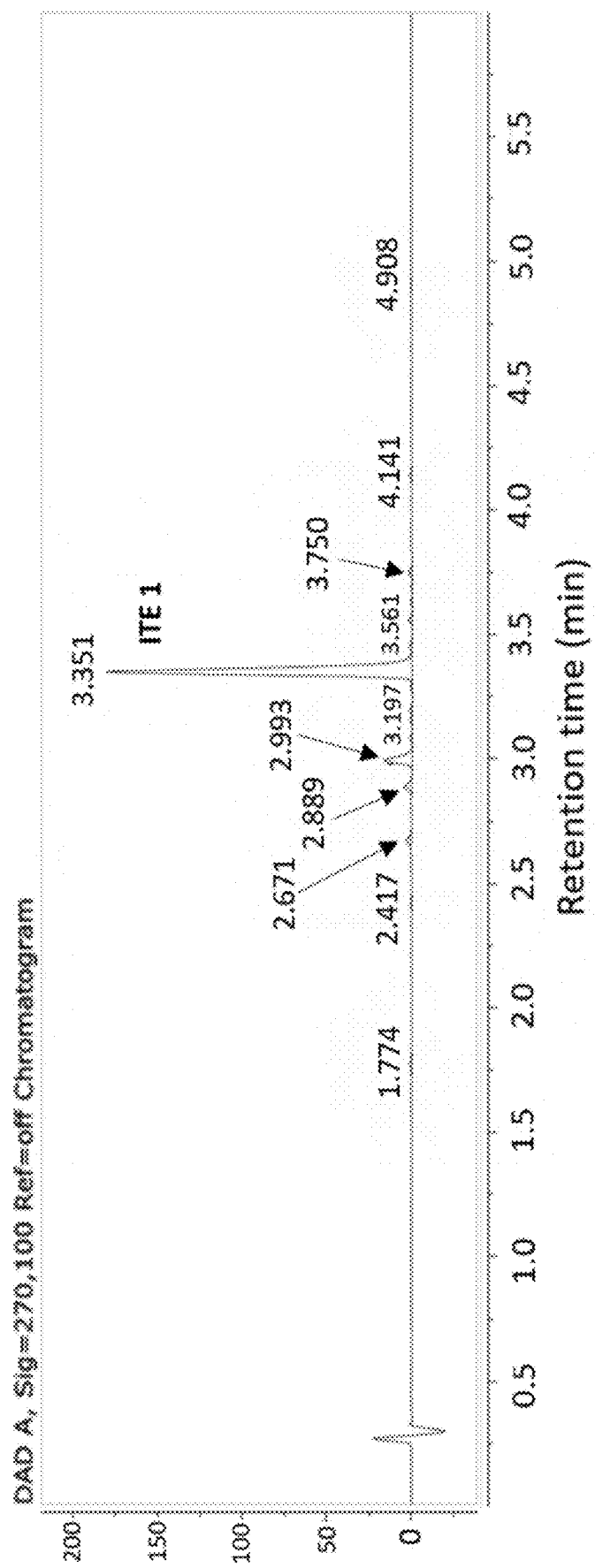
FIG. 5 shows an HPLC chromatogram of $SiO_2$ purified ITE (1).

The residue was purified in two stages. The first was involved purification by $SiO_2$ column chromatography (200 g $SiO_2$, 0-100% EtOAc in n-heptane or alternatively 220 g $SiO_2$, 0-100% MTBE in n-heptane). An amount of 1 g purified ITE (1) was obtained in ~80% HPLC purity by applying column chromatography with 220 g $SiO_2$, 0-100% MTBE in n-heptane (FIG. 5).

Figure 6:
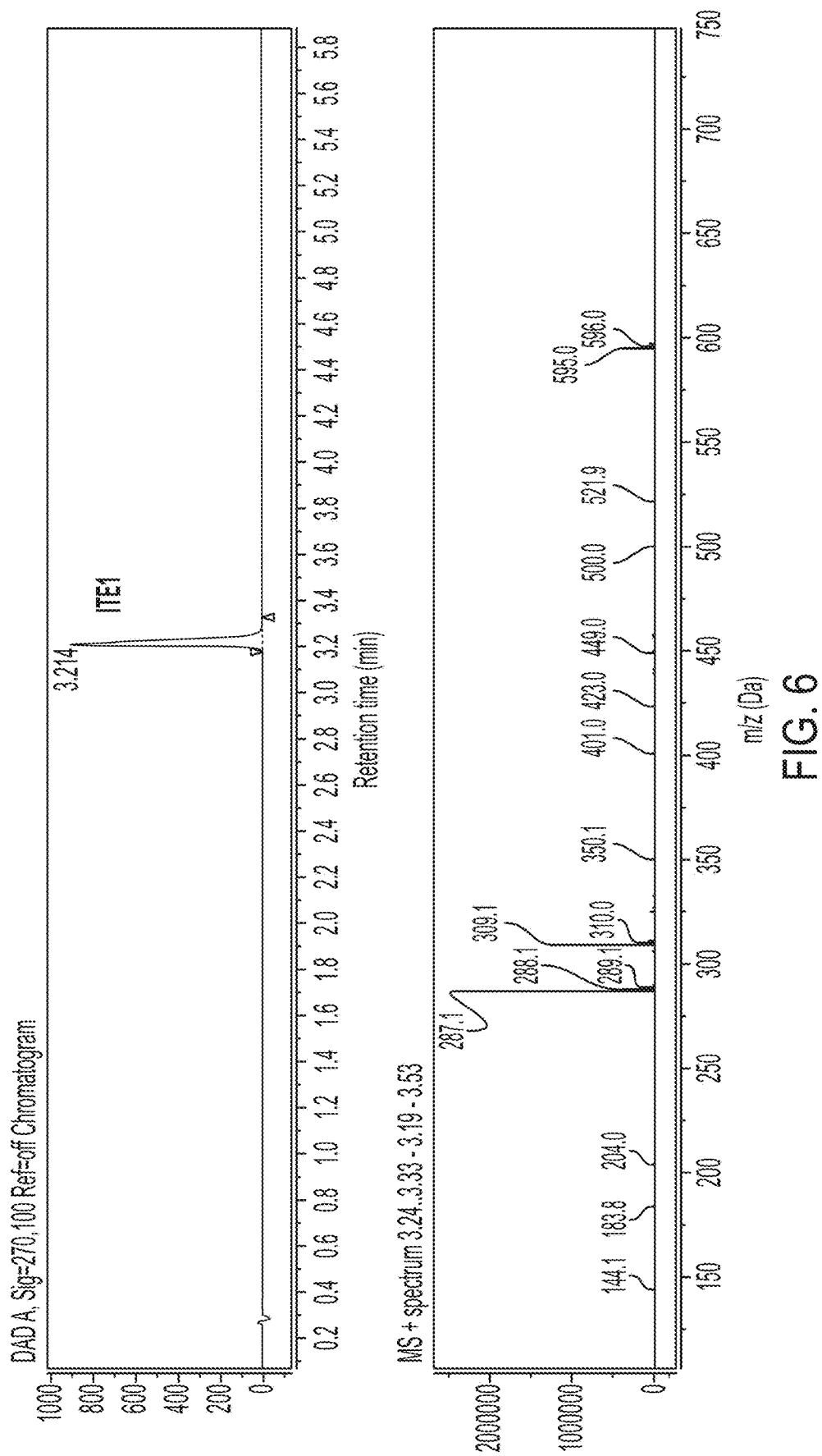
FIG. 6 shows an LCMS analysis of ITE (1) following $SiO_2$ column chromatography and preparative reversed-phase HPLC.
Figure 7:
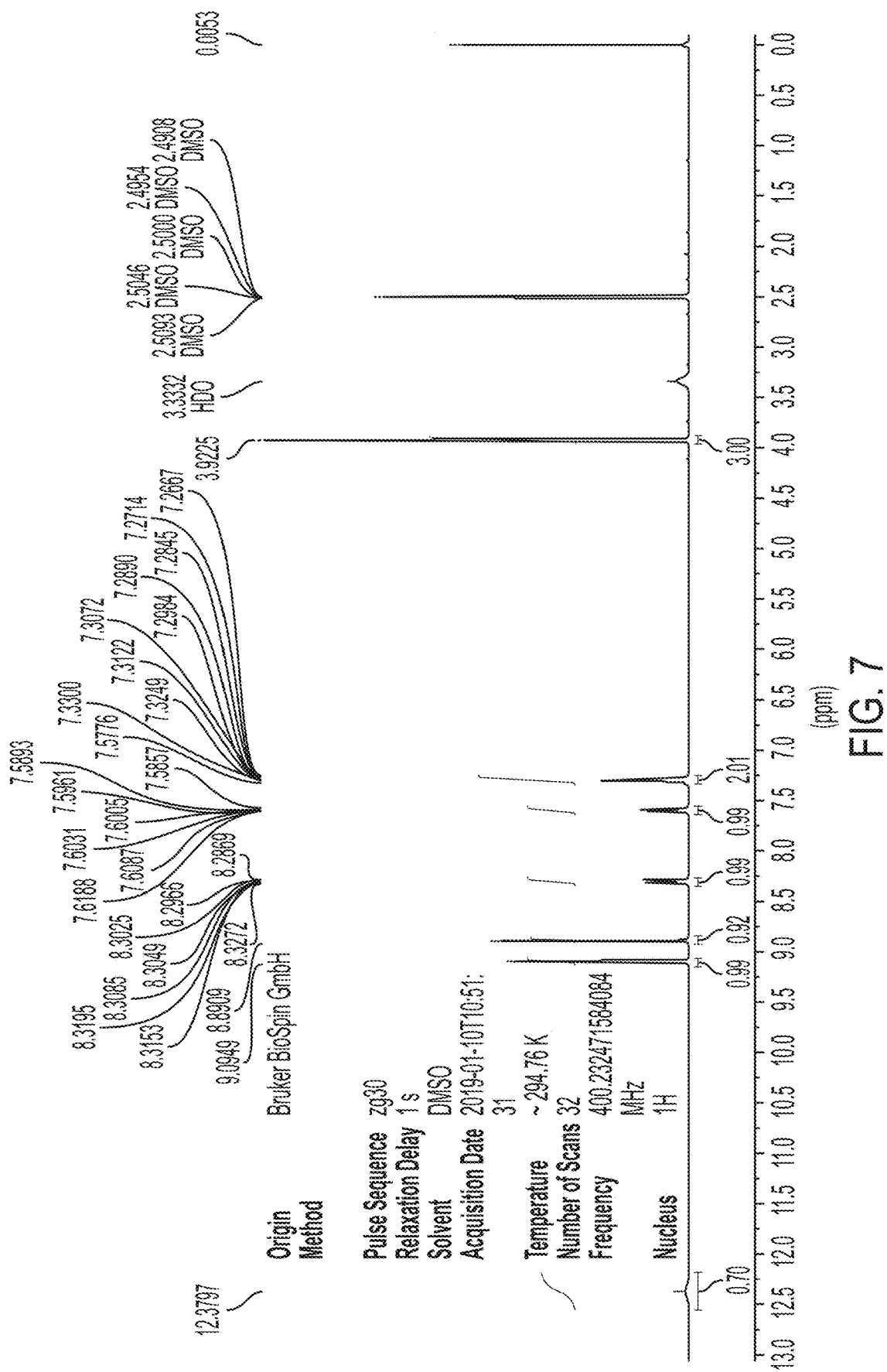
FIG. 7 shows a $^1H$ NMR spectrum (400 MHz, DMSO-d6) of ITE (1) following $SiO_2$ column chromatography and preparative reversed-phase HPLC.

The material was further purified by reversed-phase preparative HPLC. Product containing fractions were combined, concentrated, and dried in a vacuum oven (T=40° C.) for 2 d, yielding the title compound (1) as a yellow solid (0.51 g, 11%, >95% HPLC purity). The 11% yield was obtained from 47 to ITE (1). An overall ITE product yield of 6.1% was obtained applying the steps in Examples 2, 3, and 4 (from the indole carboxylic acid, 35, to ITE (1)). An LCMS analysis is shown in FIG. 6. A $^1H$ NMR spectrum is shown in FIG. 7. HPLC ($C_{18}$) $t_R$=3.36 min. LCMS (ESI$^+$, $C_{18}$) $t_R$=1.92 min, m/z=287.1 (calcd 287.1 for [M+H]$^+$. $^1H$ NMR (400 MHz, DMSO-d$_6$) δ12.38 (s, br, 1H), 9.09 (s, 1H), 8.89 (s, 1H), 8.42-8.19 (m, 1H), 7.76-7.50 (m, 1H), 7.39-7.16 (m, 2H), 3.92 (s, 3H).

Example 5

Preliminary Base Screening Experiments for Preparing Metallated Thiazole-4-Carboxylic Acid For the Weinreb ketone synthesis of amide 47, an initial selection of bases was tested for the metalation of the thiazole moiety, i.e. n-BuLi, iPrMgCl.LiCl (Turbo Grignard), LiHMDS, NaHMDS, and KHMDS. First, n-BuLi and iPrMgCl.LiCl were tested in the preparation of metallated 50 (the Grignard). The results are provided in Table 1. Scheme 2 shows an exemplary reaction for this procedure.

Scheme 2

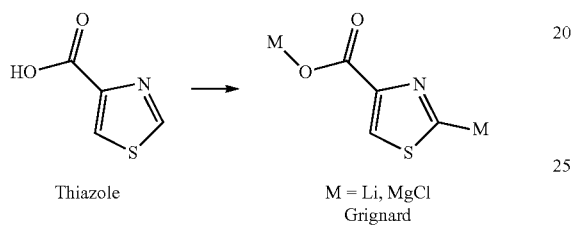

Thiazole      M = Li, MgCl Grignard

TABLE 1

Preliminary Base Screening Results for Metalation of 50

| Exp. | Base (equiv.) | Temperature (° C.) | Reaction Time (min) | Thiazole * | Grignard *# |
|---|---|---|---|---|---|
| 1 | iPrMgCl•LiCl (2.2 equiv.), 10 vol. THF | −20 | 60 | 59 | 40 |
| 2 | n-BuLi (2.2 equiv.), 10 vol. THF | −20 | 60 | 25 | 0 |
| 3 | iPrMgCl•LiCl (2.2 equiv.) 15 vol. THF | −20 | 60 | 56 | 42 |
|   | (3.2 equiv.) | −20 | 120 | 39 | 47 |
|   | (3.2 equiv.) | 30 | 150 | 31 | 30 |

* HPLC area % (220-320 nm).
Detected as the corresponding isopropyl alcohol upon quenching with acetone.

When n-BuLi was used, oiling out was observed during the addition of the base. For iPrMgCl.LiCl, a Weinreb ketone synthesis was carried out using 1.1 equiv. of metallated 50 (assuming 50% conversion of the thiazole) under the following conditions: 2.2 equiv. of iPrMgCl.LiCl at −20° C. in 15 vol. THF (Scheme 3).

Scheme 3

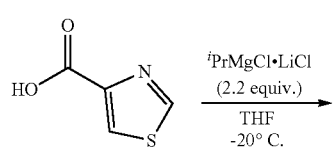

0.1 g, 0.77 mmol
2.2 equiv.
50

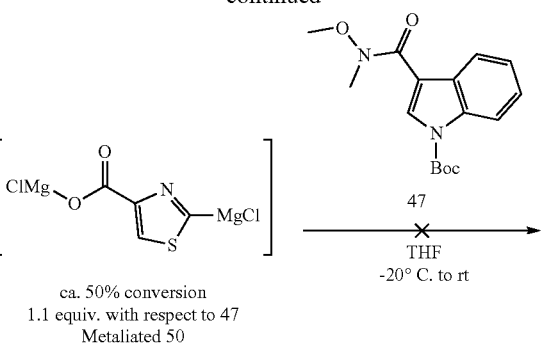

ca. 50% conversion
1.1 equiv. with respect to 47
Metaliated 50

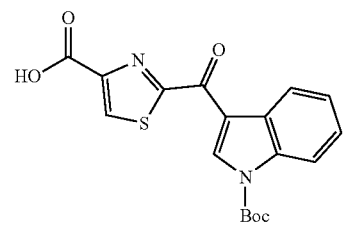

51
not observed

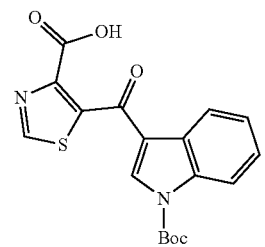

129 mg, 85% HPLC purity
tentative 54

Figure 8:
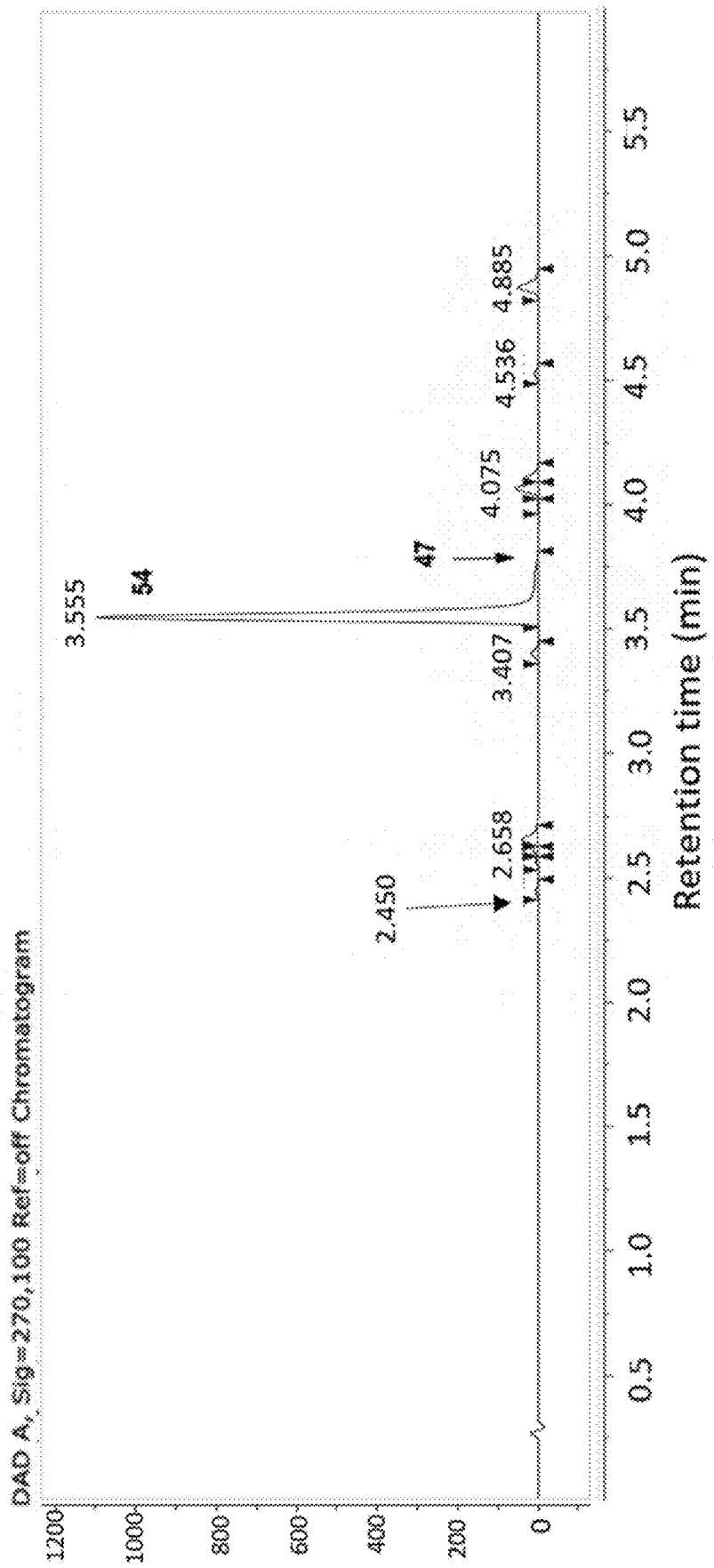
FIG. 8 shows an HPLC chromatogram (220-320 nm) of crude Boc-protected ITE acid (54).
Figure 9:
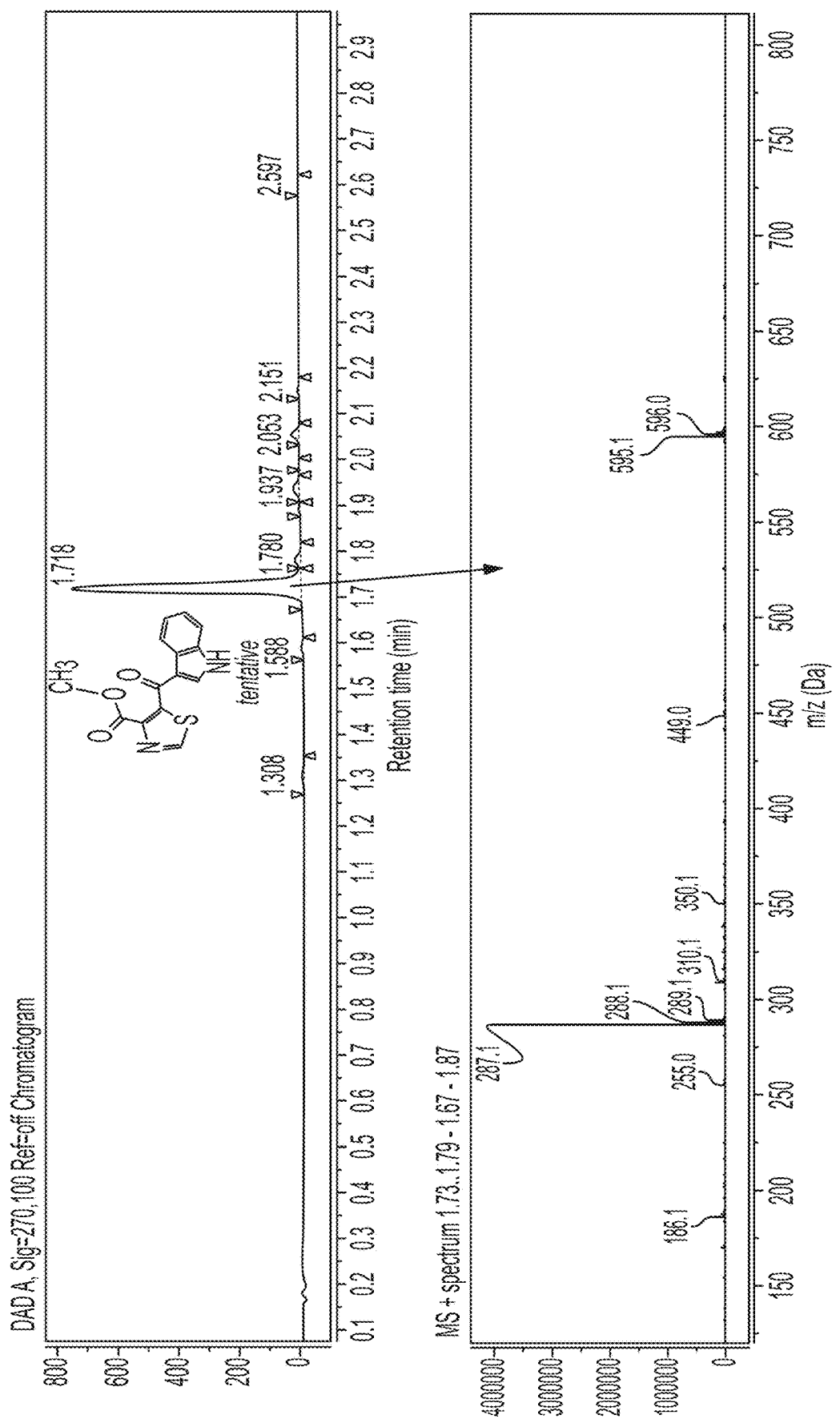
FIG. 9 shows an LCMS analysis of (54a) at t=1 hr.
Figure 10:
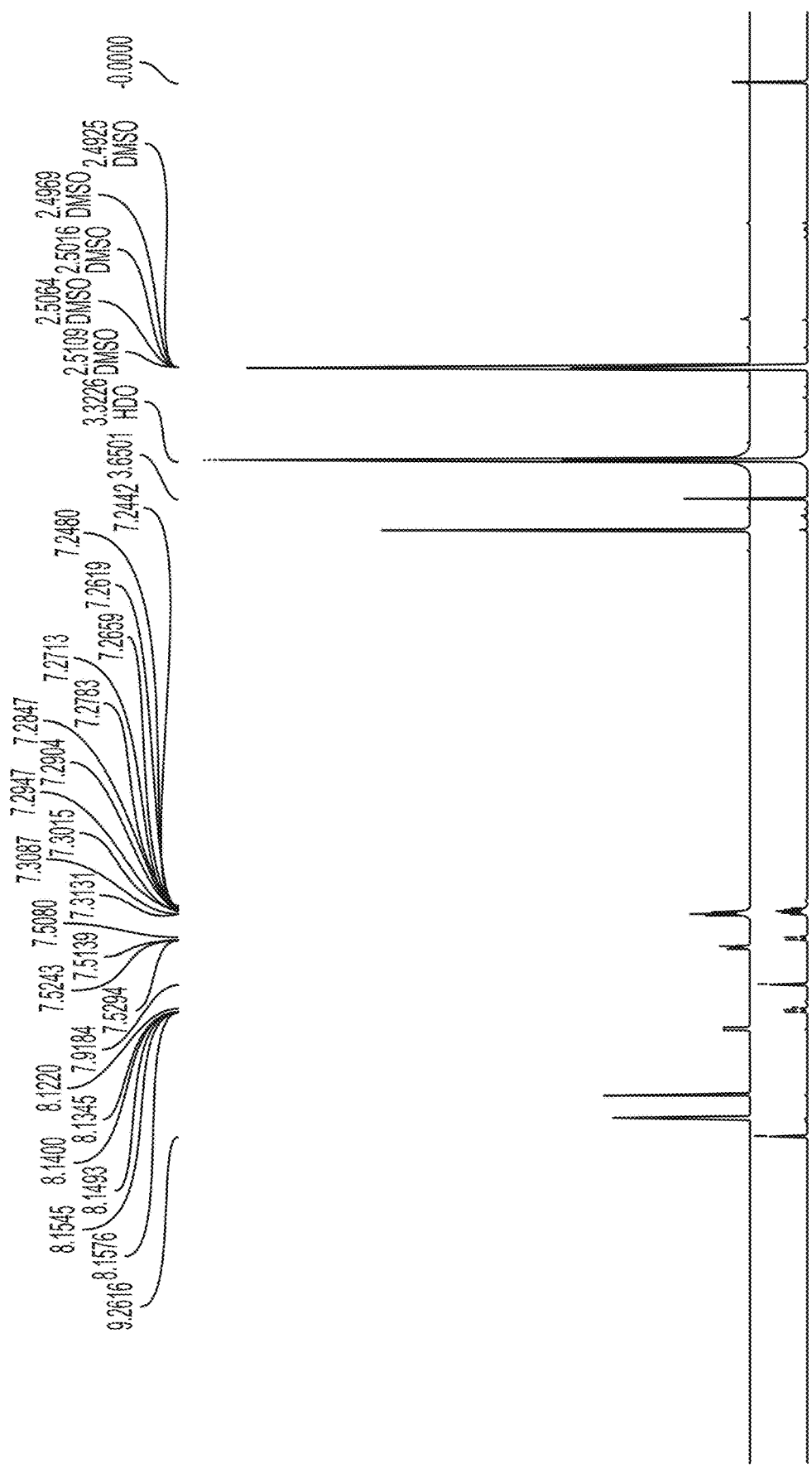
FIG. 10 shows an overlay of the $^1H$ NMR spectra (400 MHz, DMSO-d6) of ITE reference (top) and $SOCl_2$/MeOH treated tentative ITE analogue 54a (bottom).

A Grignard solution of metallated 50 in Scheme 3 above was slowly added to a solution of Weinreb amide 47 (1 equiv.) in THF (5 vol.) at −20° C. After work-up (EtOAc/aq. KHSO$_4$), complete consumption of 47 and 85 area % of tentative 54 were detected by HPLC analysis (100% isolated yield). An HPLC chromatogram is provided in FIG. 8. The material was directly tested in the deprotection/esterification reaction (Scheme 4). An aliquot of the material was treated with SOCl$_2$ (5 equiv.)/MeOH at 60° C. After complete consumption of the starting material, LCMS analysis showed the formation of a species with the desired mass (m/z=287.1) for ITE 1. However, the retention time t$_R$=1.72 min did not match the ITE reference sample (t$_R$=1.95 min, FIG. 9). Subsequent NMR analysis also showed that ITE 1 was not produced (FIG. 10).

Scheme 4

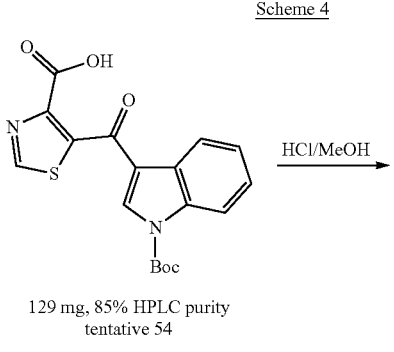

The data indicate that a regioisomer of ITE was prepared. Without wishing to be bound by theory, it is understood that the formation of the regioisomer could be a result of directed ortho metalation due to the acid moiety of the thiazole (Scheme 5).

Example 6

Metalation Experiments with 2-bromothiazole-4-carboxylic Acid as a Substrate

In another experiment to prepare a Grignard reagent from 50, 2-bromothiazole-4-carboxylic acid 55 was used as a substrate. Bromothiazole 55 was chosen to investigate Mg/Br exchange for selective metalation in the 2-position (Scheme 6).

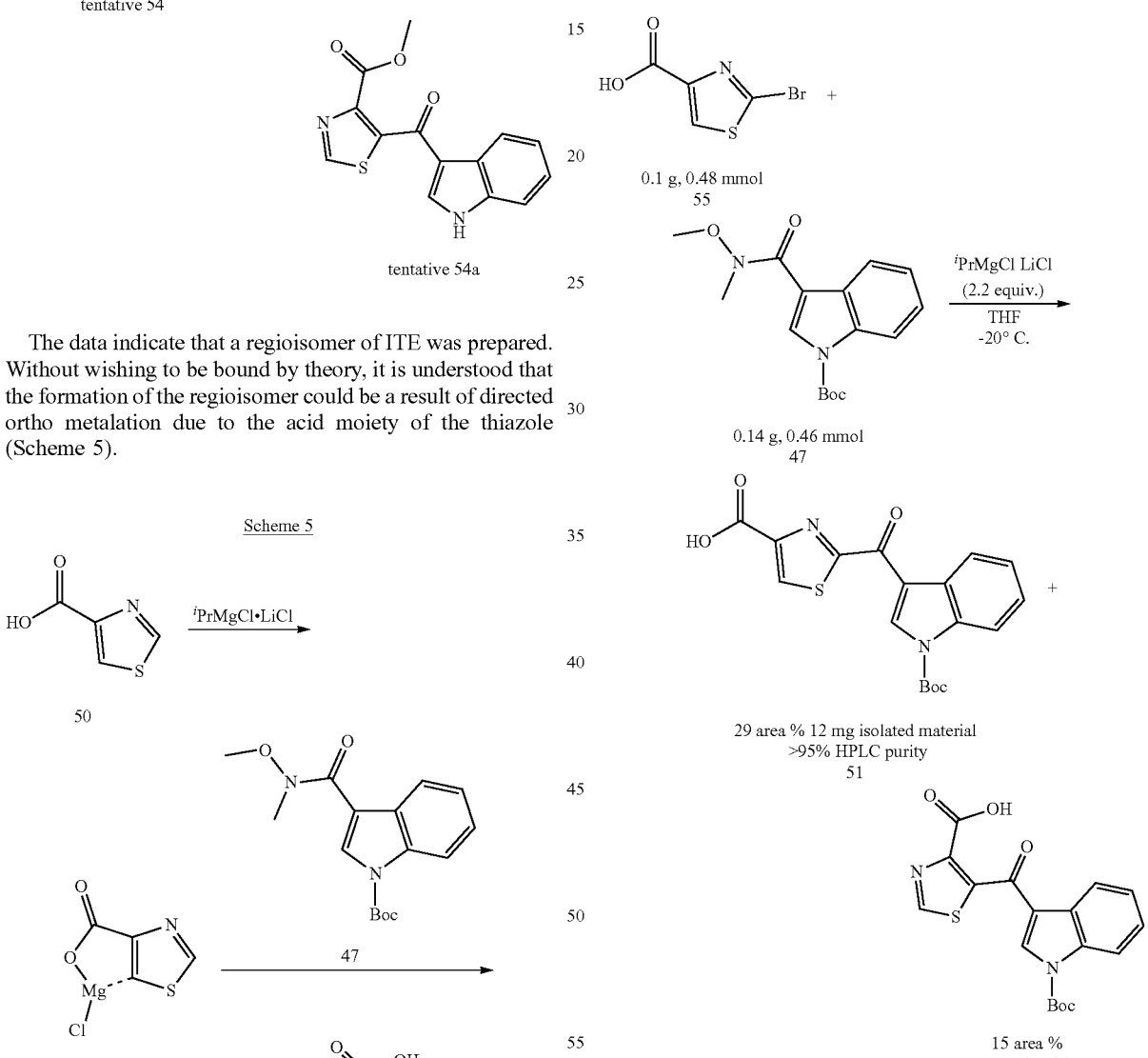

Figure 11:
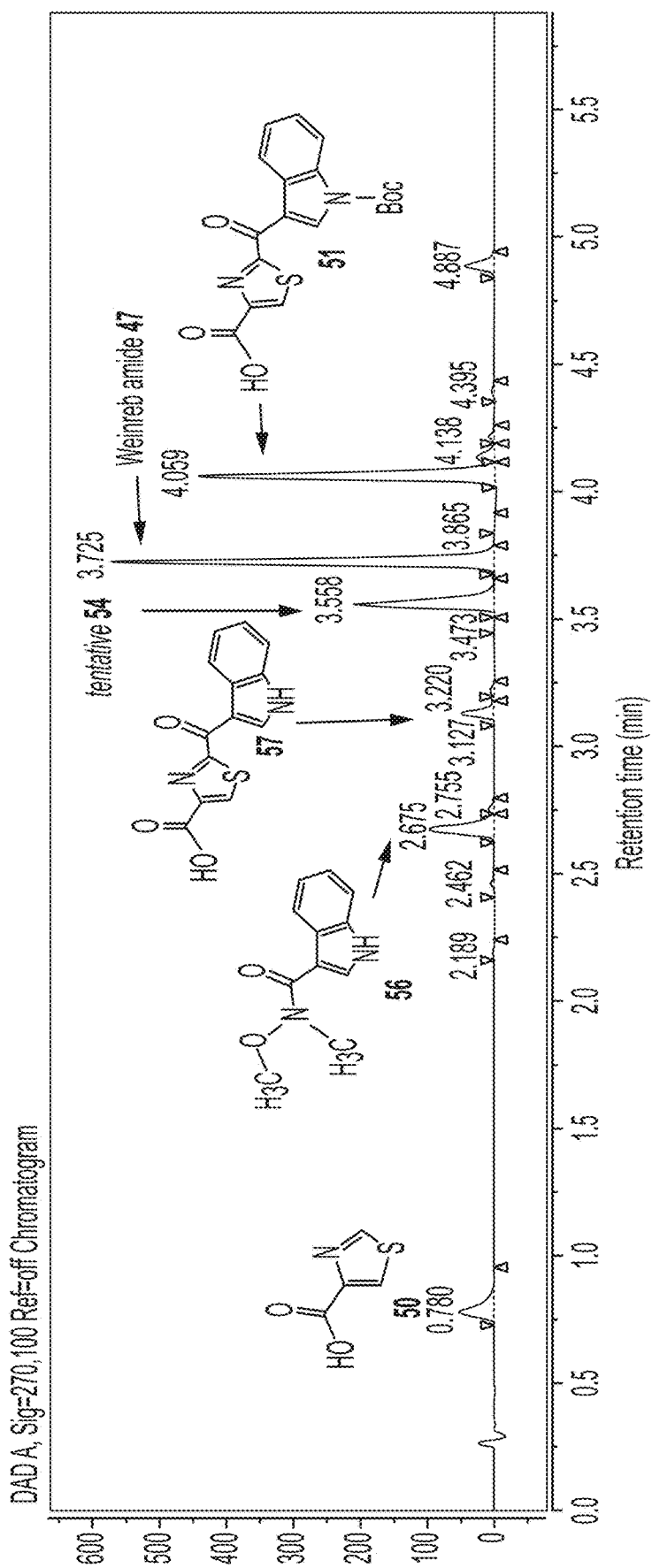
FIG. 11 shows an HPLC chromatogram of the synthesis of ITE (I) using bromothiazole (55).

In accordance with Scheme 6, 55 (1 equiv.) was treated with iPrMgCl.LiCl (2.2 equiv.) in THF (15 vol.) at −20° C. for 1 h. The obtained mixture was added to a solution of Weinreb amide 47 (0.95 equiv.) in THF (5 vol.) at −20° C. and the mixture was stirred overnight and allowed to reach room temperature. After stirring overnight, HPLC and LCMS analyses indicated an incomplete conversion, with a mixture of desired 2-susbtituted 51, undesired 5-substituted 54, and other side-products (FIG. 11).

Example 7

Investigation of Additional Bases for Selective Thiazole Functionalization

A series of HMDS bases (i.e. LiHMDS, NaHMDS, and KHMDS), were investigated for selective functionalization of the thiazole in the 2-position. The results are provided in Table 2.

TABLE 2

Analysis of HDMS Bases on Thiazole Functionalization

| Base (equiv.) | Reaction time (h) | Thiazole (50) | Boc unprotected Weinreb (56)* | Boc Unprotected (51)* | Weinreb Amide (47)* | Regioisomer (54)* | Boc ITE acid (51) |
|---|---|---|---|---|---|---|---|
| LiHMDS (2.1) | 2.5 | 1 | 19 | 1 | 35 | 18 | 13 |
| NaHMDS (2.8) | 2.5 | 3 | 15 | 10 | 1 | 9 | 49 |
| KHMDS (3) | 2.5 | 5 | 22 | 1 | 42 | 0 | 16 |

*HPLC area % (220-320 nm).

From the experiments, it was concluded that a larger cation could reduce the deprotonation of 50 in the 5-position and, for KHMDS, no side-product 54 was detected. Furthermore, a slower addition of the base resulted in pronounced Boc deprotection.

Example 8

Experimental Synthetic Reactions

Tests were run to investigate several synthetic pathways for the preparation of ITE. They are highlighted below.

Experiment A, "Vilsmeier Route." Starting from a cysteine derivative, a trityl protected amide was formed followed by a dehydrative cyclization and an oxidation to yield a thiazole amide intermediate. The thiazole amide intermediate was then used in a Vilsmeier-Haack reaction with an indole to produce ITE. Low yields were obtained from the synthesis, as well as difficult removal of byproducts in a dehydrative cyclization/oxidation sequence. Additionally, an unclean conversion was observed in the final Vilsmeier reaction.

Experiment B, "Friedel Crafts Route." A trityl protected cysteine derivative was reacted with a sterically hindered acid chloride to generate a trityl protected amide. The trityl protected amide was then transformed into a thiazole through dehydration and oxidation reactions. The thiazole then underwent deprotection, followed by a Friedel-Crafts reaction with an indole to generate ITE. Low yields and unidentifiable side products were obtained by this method.

Experiment C, "Regel Route." First, an indole acid was protected and then transformed into a protected indole acid chloride. Following this, the acid chloride was further converted into a protected ITE analogue with a thiazole building block, After deprotection, ITE was obtained. This route required cryogenic conditions in several steps and provided low ITE yields.

Experiment D, "Weinreb I." Starting from a protected indole acid, the corresponding protected Weinreb amide was reacted with a methyl ester-functionalized halothiazole Grignard. ITE was obtained following deprotection. LCMS analysis indicated incomplete conversion of the reaction and the generation of side products.

Experiment E, "Weinreb III." An unprotected Weinreb amide was prepared from indole-3-carboxylic acid and was reacted with a thiazole acid to produce ITE acid. After contact with an acid, ITE was obtained. Reactions yielded thick suspensions and low ITE yields.

Efforts have been made to ensure accuracy with respect to numbers used (e.g. amounts, temperature, etc.) but some experimental errors and deviations should be accounted for.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Unless defined otherwise, technical and scientific terms used herein have the same meaning as commonly understood by one of ordinary skill in the art to which this subject matter belongs, and are consistent with: Singleton et al (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

The disclosures of all cited references including publications, patents, and patent applications are expressly incorporated herein by reference in their entirety.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller ranges is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation. One skilled in the art will recognize many methods and materials similar or equivalent to those described herein, which could be used in the practicing the subject matter described herein. The present disclosure is in no way limited to just the methods and materials described.

What is claimed is:
1. A process for the preparation of a compound of Formula I:

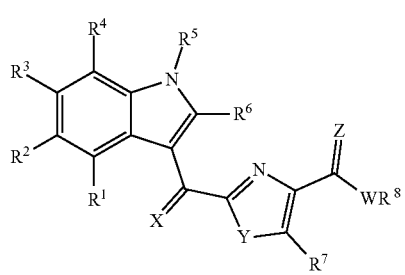

wherein, W, X, Y, and Z are each independently selected from the group consisting of O, S, and NH;
$R^1$, $R^2$, $R^3$, $R^4$, $R^5$, $R^6$, $R^7$, and $R^8$ are each independently selected from the group consisting of hydrogen, deuterium, halo, amino, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, heterocyclyl, and —S(O)$_n$R$^9$ (n=0 to 2, R$^9$ is directly connected to S), wherein R$^9$ is selected from the group consisting of hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, aryl, heteroaryl, cycloalkyl, and heterocyclyl;

the process comprising:
contacting a compound of formula (II) with a protecting group in the presence of a nucleophile to prepare a compound of formula (III);

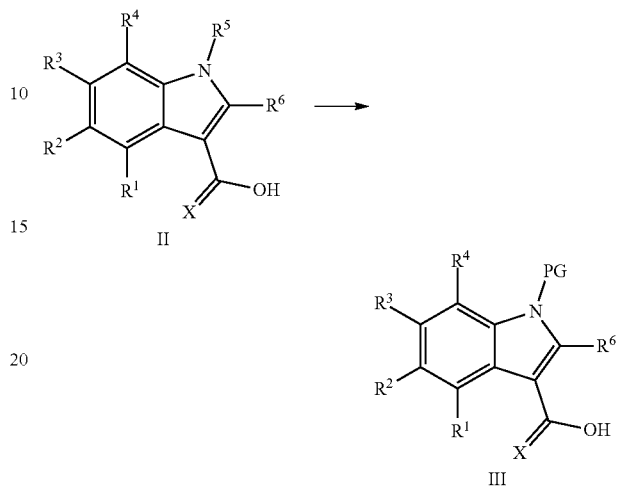

where PG is a protecting group;
contacting the compound of formula (III) with a halogenating agent, followed by an amine to prepare a compound of formula (IV);

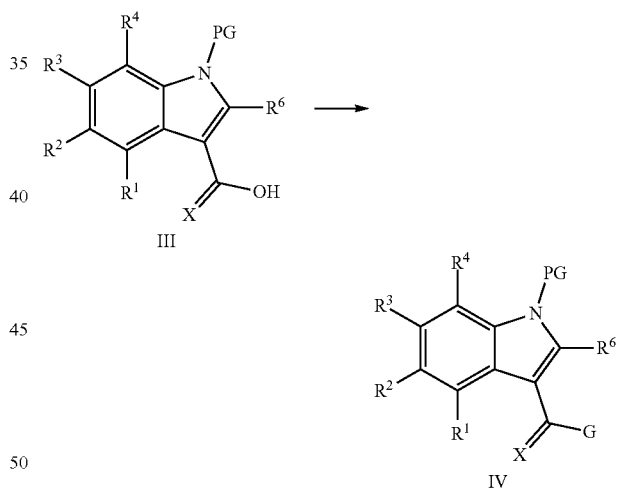

where G is selected from the group consisting of

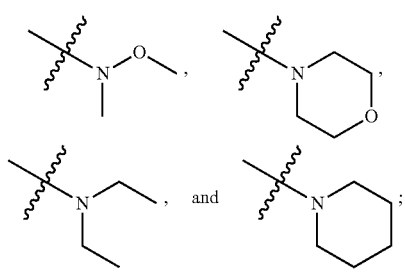

contacting the compound of formula (IV) with a compound of formula (V) in the presence of a base (b-d) and a solvent (s-d) to prepare a compound of formula (VI); and

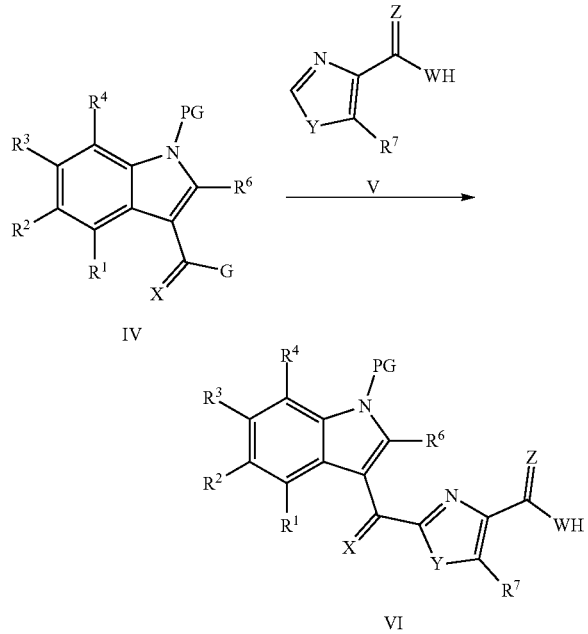

contacting the compound of formula (VI) with an acid; wherein, the compound of Formula I is prepared.

2. The process of claim 1, wherein said protecting group (PG) is selected from the group consisting of allyl carbamate (Alloc), t-butyl carbamate (BOC), 9-fluorenylmethyl carbamate (FMOC), benzyl carbamate (Cbz), acetamide, chloroacetamide, trifluoroacetamide (TFA), phthalimide, benzylamine, triphenylmethylamine (tritylamine), benzylideneamine, p-toluenesulfonamide, and tosylamide.

3. The process of claim 1, wherein said nucleophile is selected from the group consisting of 1,4-Diazabicyclo[2.2.2]octane (DABCO), quinuclidine, N-Methylpiperidine, N-methylmorpholine, and 4-dimethylaminopyridine (DMAP).

4. The process of claim 1, wherein G is

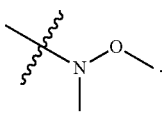 [SMILES: *N(C)OC]

5. The process of claim 1, wherein prior to said contacting the compound of formula (II) with the protecting group in the presence of the nucleophile, said compound of formula (II) is contacted with a solvent (s-a) and a base (b-a) to form a mixture.

6. The process of claim 5, wherein said solvent (s-a) is selected from the group consisting of ethyl acetate, DMF, DMSO, dichloromethane, toluene, isopropyl acetate, acetonitrile, and acetone; and, said base (b-a) is selected from the group consisting of diisopropylethylamine, pyridine, triethylamine, and 2,6-di-tert-butylpyridine.

7. The process of claim 1, wherein said halogenating agent is a chlorination agent.

8. The process of claim 1, wherein said amine is N-Methoxymethanamine.

9. The process of claim 1, wherein said contacting the compound of formula (III) with said halogenating agent is in the presence of a solvent (s-b).

10. The process of claim 9, wherein the solvent (s-b) is selected from the group consisting of dichloromethane, diethyl ether, chloroform, 1,4-dioxane, toluene, pentane, cyclopentane, hexane, and benzene.

11. The process of claim 1, wherein said contacting with an amine to prepare a compound of formula IV is in the presence of a solvent (s-c) and a base (b-c).

12. The process of claim 11, wherein said solvent (s-c) is selected from the group consisting of tetrahydrofuran, ethyl acetate, dichloromethane, ethanol, methanol, acetone, methyl ethyl ketone, isopropanol, n-propanol, acetonitrile, and dimethyl sulfoxide, and, said base (b-c) is selected from the group consisting of diisopropylethylamine, pyridine, triethylamine, and 2,6-di-tert-butylpyridine.

13. The process of claim 1, wherein said base (b-d) is selected from the group consisting of potassium bis(trimethylsilyl)amide, lithium bis(trimethylsilyl)amide, lithium diisopropylamide, sodium bis(trimethylsilyl)amide, sodium tert-butoxide, and potassium tert-butoxide.

14. The process of claim 1, wherein said solvent (s-d) is selected from the group consisting of tetrahydrofuran, ethyl acetate, dichloromethane, ethanol, methanol, acetone, methyl ethyl ketone, isopropanol, n-propanol, acetonitrile, and dimethyl sulfoxide.

15. The process of claim 1, wherein said acid is selected from the group consisting of hydrochloric acid, sulfuric acid, and nitric acid.

16. The process of claim 1, wherein W, X, Y, and Z are each independently O or S.

17. The process of claim 1, wherein $R^1$, $R^2$, $R^3$, $R^4$, $R^5$, $R^6$, $R^7$, and $R^8$ are each independently selected from the group consisting of hydrogen, $C_1$-$C_6$ alkyl, halo, $C_1$-$C_6$ haloalkyl, and alkoxy.

18. The process of claim 17, wherein $R^1$, $R^2$, $R^3$, $R^4$, $R^5$, $R^6$, $R^7$, and $R^8$ are each independently selected from the group consisting of hydrogen, methyl, ethyl, and propyl.

19. The process of claim 1, wherein the compound of Formula I is a compound having a structure:

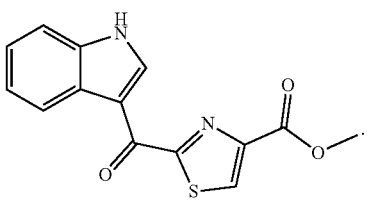 [SMILES: COC(=O)c1csc(C(=O)c2c[nH]c3ccccc23)n1]

20. The process of claim 19, wherein the compound of Formula I has a purity above about 93% by HPLC.

* * * * *